US008591886B2

(12) United States Patent
Ponath et al.

(10) Patent No.: US 8,591,886 B2
(45) Date of Patent: Nov. 26, 2013

(54) COMBINATION THERAPIES EMPLOYING GITR BINDING MOLECULES

(75) Inventors: Paul Ponath, San Francisco, CA (US); Michael Rosenzweig, Boston, MA (US); Jose F. Ponte, Quincy, MA (US)

(73) Assignee: GITR, Inc., Cambridge, MA (US)

( * ) Notice: Subject to any disclaimer, the term of this patent is extended or adjusted under 35 U.S.C. 154(b) by 0 days.

(21) Appl. No.: 12/218,187

(22) Filed: Jul. 11, 2008

(65) Prior Publication Data
US 2009/0136494 A1 May 28, 2009

Related U.S. Application Data

(60) Provisional application No. 60/959,246, filed on Jul. 12, 2007, provisional application No. 61/001,021, filed on Oct. 30, 2007, provisional application No. 61/126,431, filed on May 5, 2008.

(51) Int. Cl.
*A61K 39/395* (2006.01)

(52) U.S. Cl.
USPC ........................................ 424/130.1

(58) Field of Classification Search
None
See application file for complete search history.

(56) References Cited

U.S. PATENT DOCUMENTS

| | | | |
|---|---|---|---|
| 4,399,216 A | 8/1983 | Axel et al. | |
| 4,444,878 A | 4/1984 | Paulus | |
| 4,510,245 A | 4/1985 | Cousens et al. | |
| 4,634,665 A | 1/1987 | Axel et al. | |
| 4,683,195 A | 7/1987 | Mullis et al. | |
| 4,683,202 A | 7/1987 | Mullis | |
| 4,704,362 A | 11/1987 | Itakura et al. | |
| 4,741,900 A | 5/1988 | Alvarez et al. | |
| 4,745,055 A | 5/1988 | Schenk et al. | |
| 4,800,159 A | 1/1989 | Mullis et al. | |
| 4,816,397 A | 3/1989 | Boss et al. | |
| 4,816,567 A | 3/1989 | Cabilly et al. | |
| 4,965,188 A | 10/1990 | Mullis et al. | |
| 4,968,615 A | 11/1990 | Koszinowski et al. | |
| 5,168,062 A | 12/1992 | Stinski | |
| 5,179,017 A | 1/1993 | Axel et al. | |
| 5,225,539 A | 7/1993 | Winter | |
| 5,304,489 A | 4/1994 | Rosen | |
| 5,530,101 A | 6/1996 | Queen et al. | |
| 5,569,825 A | 10/1996 | Lonberg et al. | |
| 5,585,089 A | 12/1996 | Queen et al. | |
| 5,585,097 A | 12/1996 | Bolt et al. | |
| 5,589,369 A | 12/1996 | Seidman et al. | |
| 5,591,669 A | 1/1997 | Krimpenfort et al. | |
| 5,658,570 A | 8/1997 | Newman et al. | |
| 5,693,761 A | 12/1997 | Queen et al. | |
| 5,693,762 A | 12/1997 | Queen et al. | |
| 5,693,780 A | 12/1997 | Newman et al. | |
| 5,741,957 A | 4/1998 | Deboer et al. | |
| 5,756,096 A | 5/1998 | Newman et al. | |
| 5,811,524 A | 9/1998 | Brams et al. | |
| 5,837,821 A | 11/1998 | Wu | |
| 5,849,992 A | 12/1998 | Meade et al. | |
| 5,892,019 A | 4/1999 | Schlom et al. | |
| 5,939,598 A | 8/1999 | Kucherlapati et al. | |
| 5,959,083 A | 9/1999 | Bosslet et al. | |
| 5,969,108 A | 10/1999 | McCafferty et al. | |
| 6,075,181 A | 6/2000 | Kucherlapati et al. | |
| 6,111,090 A | 8/2000 | Gorman et al. | |
| 6,150,584 A | 11/2000 | Kucherlapati et al. | |
| 6,180,370 B1 | 1/2001 | Queen et al. | |
| 6,420,140 B1 | 7/2002 | Hori et al. | |
| 6,458,592 B1 | 10/2002 | Jakobovits et al. | |
| 6,476,198 B1 | 11/2002 | Kang | |
| 6,503,184 B1 | 1/2003 | Ni et al. | |
| 6,509,173 B1 | 1/2003 | Ni et al. | |
| 6,689,607 B2 | 2/2004 | Ni et al. | |
| 7,025,962 B1 | 4/2006 | Gorman et al. | |
| 2002/0103345 A1 | 8/2002 | Zhu | |
| 2002/0150993 A1 | 10/2002 | Ashkenazi et al. | |
| 2003/0133936 A1 | 7/2003 | Byrne et al. | |
| 2003/0138426 A1 | 7/2003 | Ni et al. | |
| 2003/0153499 A1 | 8/2003 | Ni et al. | |
| 2004/0157786 A1 | 8/2004 | Bissery | |
| 2005/0014224 A1* | 1/2005 | Collins et al. | 435/69.1 |
| 2005/0048054 A1 | 3/2005 | Hanabuchi et al. | |
| 2005/0054829 A1* | 3/2005 | Wiley et al. | 530/351 |
| 2005/0069983 A1 | 3/2005 | Ashkenazi et al. | |
| 2005/0180971 A1* | 8/2005 | Ashdown | 424/144.1 |
| 2005/0202008 A1 | 9/2005 | Williams et al. | |
| 2005/0238628 A1 | 10/2005 | Blau | |
| 2006/0002932 A1 | 1/2006 | Vieweg | |
| 2006/0051350 A1 | 3/2006 | Van Oosterhout et al. | |
| 2006/0057111 A1* | 3/2006 | Hedlund et al. | 424/93.1 |
| 2006/0099171 A1 | 5/2006 | Tone et al. | |
| 2006/0134102 A1 | 6/2006 | LePage et al. | |

(Continued)

FOREIGN PATENT DOCUMENTS

EP    0 068 763    4/1987
EP    0 255 694    2/1988

(Continued)

OTHER PUBLICATIONS

Paul, Fundamental Immunology, 3rd Edition, 1993, pp. 292-295.*
Rudikoff et al(Proc. Natl. Acad. Sci. USA 1982 vol. 79: p. 1979).*
Pascalis et al (The Journal of Immunology (2002) 169, 3076-3084).*
Casset et al. (2003) BBRC 307, 198-205,.*
Wiesenthal (http://weisenthal.org/feedback. html, Feb. 4, 2002).*
Tallarida (Drug Synergism and Dose-effect Analysis, Chapman & Hall/CRC, Boca Raton, 2000, pp. 1-13).*
Berenbaum ("Synergy, additivism and antagonism in immunosuppression," Clin exp Immunol 28:1-18, 1977).*
Stedman's Medical Dictionary, 28th Ed. (2005), 1 page.*
GenBank Accession No. gi40354198 dated Sep. 3, 2007.
GenBank Accession No. gi23238190 dated Apr. 11, 2010.
GenBank Accession No. gi23238193 dated Apr. 11, 2010.
GenBank Accession No. gi23238196 dated Apr. 19, 2010.
Adelman et al., "In Vitro Deletional Mutagenesis for Bacterial Production of the 20,000-Dalton Form of Human Pituitary Growth Hormone," *DNA*, 1983, 2(3):183-193.
Amit et al., "Three-Dimensional Structure of an Antigen-Antibody Complex at 2.8 Å Resolution," *Science*, 1986, 233:747-753.
Arthur and Mason, "T Cells That Help B Cell Responses to Soluble Antigen Are Distinguishable from Those Producing Interleukin 2 on Mitogenic or Allogeneic Stimulation," *J Exp Med*, 1986, 163:774-786.

(Continued)

*Primary Examiner* — Sheela J Huff
(74) *Attorney, Agent, or Firm* — Fish & Richardson P.C.

(57) ABSTRACT

The present invention provides combination therapies that employ a GITR binding molecule in combination with one or more additional agents.

10 Claims, 8 Drawing Sheets

(56) References Cited

U.S. PATENT DOCUMENTS

| | | | |
|---|---|---|---|
| 2006/0135756 | A1 | 6/2006 | Gorman et al. |
| 2006/0141573 | A1 | 6/2006 | Ashkenazi et al. |
| 2006/0281146 | A1 | 12/2006 | Bodary et al. |
| 2007/0098719 | A1* | 5/2007 | Smith et al. ............... 424/144.1 |
| 2007/0178093 | A1 | 8/2007 | Hanabuchi et al. |
| 2007/0184444 | A1 | 8/2007 | Abbas et al. |
| 2007/0185017 | A1 | 8/2007 | Aggarwal et al. |
| 2008/0220000 | A1 | 9/2008 | Moore et al. |

FOREIGN PATENT DOCUMENTS

| | | |
|---|---|---|
| EP | 0 125 023 | 6/1991 |
| EP | 0 120 694 | 7/1993 |
| EP | 0 368 684 | 3/1994 |
| EP | 0 266 663 | 1/1995 |
| EP | 0 256 654 | 9/1996 |
| EP | 1 196 186 | 10/2007 |
| EP | 0 920 505 | 6/2008 |
| JP | 2006-522087 A | 9/2006 |
| WO | WO 87/02671 | 5/1987 |
| WO | WO 88/03559 | 5/1988 |
| WO | WO 88/03565 | 5/1988 |
| WO | WO 90/07861 | 7/1990 |
| WO | WO 92/22653 | 12/1992 |
| WO | WO 94/09817 | 5/1994 |
| WO | WO 98/24895 | 6/1998 |
| WO | WO 99/40196 | 8/1999 |
| WO | WO 00/06605 | 2/2000 |
| WO | WO 00/37504 | 6/2000 |
| WO | WO 00/58499 | 10/2000 |
| WO | WO 00/76310 | 12/2000 |
| WO | WO 02/02781 | 1/2002 |
| WO | WO 03/006058 | 1/2003 |
| WO | WO 03/009865 | 2/2003 |
| WO | WO 03/049758 | 6/2003 |
| WO | 2004/087152 | 10/2004 |
| WO | WO 2004/084942 | 10/2004 |
| WO | WO 2004/107618 | 12/2004 |
| WO | 0007190 * | 1/2005 |
| WO | WO 2005/007190 | 1/2005 |
| WO | WO 2006/078911 | 7/2006 |
| WO | WO 2006/105021 A2 | 10/2006 |
| WO | WO 2006/132272 | 12/2006 |
| WO | WO 2007/084775 | 7/2007 |
| WO | WO 2007/133822 | 11/2007 |

OTHER PUBLICATIONS

Askari and McDonnell, "Antisense-oligonucleotide therapy," *N Eng J Med*, 1996, 334:316-318.
Balint and Larrick, "Antibody engineering by parsimonious mutagenesis," *Gene*, 1993, 137:109-118.
Barbas III et al., "Semisynthetic combinatorial antibody libraries: a chemical solution to the diversity problem," *Proc Natl Acad Sci USA*, 1992, 89(10):4457-4461.
Benhar and Pastan, "Cloning, expression and characterization of the Fv fragments of the anti-carbohydrate mAbs B1 and B5 as single-chain immunotoxins," *Protein Eng*, 1994, 7(12):1509-1515.
Bennett and Schwartz, "Antisense therapy for angioplasty restenosis. Some critical considerations," *Circulation*, 1995, 92(7):1981-1983.
Berenbaum, "Synergy, additivism and antagonism in immunosuppression," *Clin. Exp. Immunol.*, 1977, 28:1-18.
Biacore X100—Readily accessible protein interaction analysis—in your lab, GE Healthcare, 2007.
Bird et al., "Single-Chain Antigen-Binding Proteins," *Science*, 1988, 242:423-426.
Boder et al., "Directed evolution of antibody fragments with monovalent femtomolar antigen-binding affinity," *Proc Natl Acad Sci USA*, 2000, 97(20):10701-10705.
Boder and Wittrup, "Yeast surface display for screening combinatorial polypeptide libraries," *Nat. Biotechnol*, 1997, 15(6):553-557.
Bushman, "RNA interference: applications in vertebrates," *Mol Ther*, 2003, 7:9-10.

Byrn et al., "Biological properties of a CD4 immunoadhesin," *Nature*, 1990, 344:667-670.
Cadwell and Joyce, "Randomization of genes by PCR mutagenesis," *PCR Meth Appl*, 1992, 2:28-33.
Cadwell and Joyce, "Mutagenic PCR," *PCR Meth Appl*, 1994, 3(6):S136-S140.
Casset et al., "A peptide mimetic of an anti-CD4 monoclonal antibody by rational design," *Biochem Biophys Res Commun*, 2003, 307:198-205.
Chamow and Ashkenazi, "Immunoadhesins: principles and applications," *Trends Biotechnol*, 1996, 14:52-60.
Cheung et al., "Epitope-Specific Antibody Response to the Surface Antigen of Duck Hepatitis B Virus in Infected Ducks," *Virology*, 1990, 176:546-552.
Chothia and Lesk, "Canonical Structures for the Hypervariable Regions of Immunoglobulins," *J Mol Biol*, 1987, 196:901-917.
Clackson et al., "Making antibody fragments using phage display libraries," *Nature*, 1991, 352:624-628.
Co et al., "Chimeric and humanized antibodies with specificity for the CD33 antigen," *J Immunol*, 1992, 148:1149-1154.
Connolly, "Analytical Molecular Surface Calculation," *J Appl Cryst*, 1983, 16:548-558.
Cottrell and Doering, "Silence of the strands: RNA interference in eukaryotic pathogens," *Trends Microbiol*, 2003, 11:37-43.
Daugherty et al., "Flow cytometric screening of cell-based libraries," *J Immunol Meth*, 2000, 243:211-227.
Davies and Riechmann, "Affinity improvement of single antibody VH domains: residues in all three hypervariable regions affect antigen binding," *Immunotechnol*, 1996, 2:169-179.
de Kruif et al., "Selection and application of human single chain Fv antibody fragments from a semi-synthetic phage antibody display library with designed CDR3 regions," *J Mol Biol*, 1995, 248:97-105.
Delgado et al., "Enhanced tumour specificity of an anti-carcinoembrionic antigen Fab' fragment by poly (ethylene glycol) (PEG) modification," *Br J Cancer*, 1996, 73(2):175-182.
Falkner and Zachau, "Expression of mouse immunoglobulin genes in monkey cells," *Nature*, 1982, 298:286-288.
Finkelman et al., "IL-4 is required to generate and sustain in vivo IgE responses," *J Immunol*, 1988, 141:2335-2341.
Francisco et al., "Production and fluorescence-activated cell sorting of *Escherichia coli* expressing a functional antibody fragment on the external surface," *Proc Natl Acad Sci USA*, 1993, 90(22):10444-10448.
Gautier et al., "α-DNA IV: α-anomeric and β-anomeric tetrathymidylates covalently linked to intercalating oxazolopyridocarbazole. Synthesis, physicochemical properties and poly (rA) binding," *Nucl Acids Res*, 1987, 15(16):6625-6641.
Georgiou et al., "Display of heterologous proteins on the surface of microorganisms: from the screening of combinatorial libraries to live recombinant vaccines," *Nat Biotechnol*, 1997, 15:29-34.
Goding, *Monoclonal Antibodies: Principles and Practice*, 1986, pp. 59-103.
Griffiths and Duncan, "Strategies for selection of antibodies by phage display," *Curr Opin Biotechnol*, 1998, 9:102-108
Griffiths et al., "Isolation of high affinity huan antibodies directly from large synthetic repertoires," *EMBO J*, 1994, 13:3245-3260.
Gurney et al., "Identification of a new member of the tumor necrosis factor family and its receptor, a human ortholog of mouse GITR," *Curr Biol*, 1999, 9:215-218.
Hanes et al., "Picomolar affinity antibodies from a fully synthetic naïve library selected and evolved by ribosome display," *Nat Biotechnol*, 2000, 18:1287-1292.
Hanes et al., "Ribosome display efficiently selects and evolves high-affinity antibodies in vitro from immune libraries," *Proc Natl Acad Sci USA*, 1998, 95(24):14130-14135.
Hanes and Plückthun, "In vitro selection methods for screening of peptide and protein libraries," *Curr Top Microbiol Immunol*, 1999, 243:107-122.
He and Taussig, "Antibody-ribosome-mRNA (ARM) complexes as efficient selection particles for in vitro display and evolution of antibody combining sites," *Nucl Acids Res*, 1997, 25(24):5132-5134.
Ho et al., "Site-directed mutagenesis by overlap extension using the polymerase chain reaction," *Gene*, 1989, 77:51-59.

(56) References Cited

OTHER PUBLICATIONS

Holt et al., "Domain antibodies: proteins for therapy," *Trends Biotechnol*, 2003, 21(11):484-490.
Hoogenboom and Chames, "Natural and designer binding sites made by phage display technology," *Immunol Today*, 2000, 21(8):371-378.
Hoogenboom et al., "Antibody phage display technology and its applications," *Immunotechnol*, 1998, 4:1-20.
Hoogenboom and Winter, "By-passing Immunisation. Human Antibodies from Synthetic Repertoires of Germline $V_H$ Gene Segments Rearranged in Vitro," *J Mol Biol*, 1992, 227(2):381-388.
Horton et al., "Gene splicing by overlap extension," *Meth Enzymol*, 1993, 217:270-279.
Huie et al., "Antibodies to human fetal erythroid cells from a nonimmune phage antibody library," *Proc Natl Acad Sci USA*, 2001, 98:2682-2687.
Huse et al., "Generation of a Large Combinatorial Library of the Immunoglobulin Repertoire in Phage Lambda," *Science*, 1989, 2476:1275-1281.
Huston et al., "Protein engineering of antibody binding sites: recovery of specific activity in an anti-digoxin single-chain Fv analogue produced in Escherichia coli," *Proc Natl Acad Sci USA*, 1988, 85:5879-5883.
Hwang et al., "Use of human germline genes in a CDR homology-based approach to antibody humanization," *Methods*, 2005, 36:35-42.
Imgenex, "Monoclonal Antibody GITR (Clone DTA-1) FITC Conjugate," retrieved online at: http://www.imgenex.com/antibody_details.php?catalog=IMG-5920C 2007.
Inoue et al., "Synthesis and hybridization studies on two complementary nona(2'-O-methyl) ribonucleotides," *Nucl Acids Res*, 1987, 15(15):6131-6148.
Inoue et al., "Sequence-dependent hydrolysis of RNA using modified oligonucleotide splints and RNase H," *FEBS Lett*, 1987, 215(2):327-330.
Irving et al., "Ribosome display and affinity maturation: from antibodies to single V-domains and steps towards cancer therapeutics," *J Immunol Meth*, 2001, 248:31-45.
Jendreyko et al., "Intradiabodies, Bispecific, Tetravalent Antibodies for the Simultaneous Functional Knockout of Two Cell Surface Receptors," *J Biol Chem*, 2003, 278(48):47812-47819.
Jones et al., "Replacing the complementarity-determining regions in a human antibody with those from a mouse," *Nature*, 1986, 321:522-525.
Kabat et al., "Unusual Distributions of Amino Acids in Complementarity-determining (Hypervariable) Segments of Heavy and Light Chains of Immunoglobulins and Their Possible Roles in Specificity of Antibody-combining Sites," *J Biol Chem*, 1977, 252:6609-6616.
Kanamaru et al., "Costimulation via Glucocorticoid-Induced TNF Receptor in Both Conventional and $CD25^+$ Regulatory $CD4^+$ T Cells," *J Immunol*, 2004, 172:7306-7314.
Karlsson et al., "Analyzing a kinetic titration series using affinity biosensors," *Analyt Biochem*, 2006, 349:136-147.
Kaufman and Sharp, "Amplification and Expression of Sequences Cotransfected with a Modular Dihydrofolate Reductase Complementary DNA Gene," *J Mol Biol*, 1982, 159:601-621.
Kerbel, "Vasohibin: the feedback on a new inhibitor of angiogenesis," *J Clin Invest*, 2004, 114(7):884-886.
Kettleborough et al., "Humanization of a mouse monoclonal antibody by CDR-grafting: the importance of framework residues on loop conformation," *Protein Engineering*, 1991, 4(7):773-783.
Kirkland et al., "Analysis of the fine specificity and cross-reactivity of monoclonal anti-lipid A antibodies," *J Immunol*, 1986, 137:3614-3619.
Kitamura et al., "Chemical engineering of the monoclonal antibody A7 by polyethylene glycol for targeting cancer chemotherapy," *Cancer Res*, 1991, 51(16):4310-4315.
Kitamura et al., "Polyethylene glycol modification of the monoclonal antibody A7 enhances its tumor localization," *Biochem Biophys Res Commun*, 1990, 171(3):1387-1394.
Knauf et al., "Relationship of effective molecular size to systemic clearance in rats of recombinant interleukin-2 chemically modified with water-soluble polymers," *J Biol Chem*, 1988, 263(29):15064-15070.
Ko et al., "Treatment of advanced tumors with agonistic anti-GITR mAb and its effects on tumor-infiltrating $Foxp3^+CD25^+CD4^+$ regulatory T cells," *J Exp Med*, 2005, 202(7):885-891.
Ko et al., "A Combination of Chemoimmunotherapies Can Efficiently Break Self-Tolerance and Induce Antitumor Immunity in a Tolerogenic Murine Tumor Model," *Cancer Res*, 2007, 67(15):7477-7486.
Köhler and Milstein, "Continuous cultures of fused cells secreting antibody of predefined specificity," *Nature*, 1975, 256:495-497.
Köhler, "Immunoglobulin chain loss in hybridoma lines," *Proc Natl Acad Sci USA*, 1980, 77:2197-2199.
Kohm et al., "Cutting Edge: Ligation of the Glucocorticoid-Induced TNF Receptor Enhances Autoreactive $CD4^+$ T Cell Activation and Experimental Autoimmune Encephalomyelitis," *J Immunol*, 2004, 172(8):4686-4690.
Kolbinger et al., "Humanization of a mouse anti-human IgE antibody: a potential therapeutic IgE-mediated allergies," *Protein Engineering*, 1993, 6(8):971-980.
Krebber et al., "Reliable cloning of functional antibody variable domains from hybridomas and spleen cell repertoires employing a reengineered phage display system," *J Immunol Meth*, 1997, 201:35-55.
Kwon et al., "Identification of a Novel Activation-inducible Protein of the Tumor Necrosis Factor Receptor Superfamily and Its Ligand," *J Biol Chem*, 1999, 274(10):6056-6061.
Lamminmäki et al., "Expanding the conformational diversity by random insertions to CDRH2 results in improved anti-estradiol antibodies," *J Mol Biol*, 1999, 291(3):589-602.
Larrick et al., "Rapid cloning of rearranged immunoglobulin genes from human hybridoma cells using mixed primers and the polymerase chain reaction," *Biochem Biophys Res Commun*, 1989, 160(3):1250-1256.
Lee and Richards, "The Interpretation of Protein Structures: Estimation of Static Accessibility," *J Mol Biol*, 1971, 55:379-400.
Little et al., "Of mice and men: hybridoma and recombinant antibodies," *Immunol Today*, 2000, 21(8):364-370.
Liu et al., "Towards proteome-wide production of monoclonal antibody by phage display," *J Mol Biol*, 2002, 315(5):1063-1073.
MacCallum et al., "Antibody-antigen interactions: contact analysis and binding site topography," *J Mol Biol*, 1996, 262(5):732-745.
Marks et al., "By-Passing Immunization: Building High Affinity Human Antibodies by Chain Shuffling," *Bio/Technol*, 1992, 10:779-783.
Marks et al., "By-passing Immunization. Human Antibodies from V-gene Libraries Displayed on Phage," *J Mol Biol*, 1991, 222:581-597.
Martin and Thornton, "Structural Families in Loops of Homologous Proteins: Automatic Classification, Modelling and Application to Antibodies," *J Mol Biol*, 1996, 263:800-815.
McHugh et al., "$CD4^+CD25^+$ Immunoregulatory T Cells: Gene Expression Analysis Reveals a Functional Role for the Glucocorticoid-Induced TNF Receptor," *Immunity*, 2002, 16:311-323.
McManus and Sharp, "Gene silencing in mammals by small interfering RNAs," *Nat Rev Genet*, 2002, 3(10):737-747.
Mercola and Cohen, "Antisense approaches to cancer gene therapy," *Cancer Gene Ther*, 1995, 2:47-59.
Milenic et al., "Construction, Binding Properties, Metabolism, and Tumor Targeting of a Single-Chain Fv Derived from the Pancarcinoma Monoclonal Antibody CC49," *Cancer Res*, 1991, 51:6363-6371.
Moldenhauer et al., "Identity of HML-1 Antigen on Intestinal Intraepithelial T Cells and of B-ly7 Antigen on Hairy Cell Leukaemia," *Scand J Immunol*, 1990, 32:77-82.
Morel et al., "Monoclonal Antibodies to Bovine Serum Albumin: Affinity and Specificity Determinations," *Mol Immunol*, 1988, 25:7-15.

(56) References Cited

OTHER PUBLICATIONS

Morrison et al., "Chimeric human antibody molecules: Mouse antigen-binding domains with human constant region domains," *Proc Natl Acad Sci USA*, 1984, 81:6851-6855.

Morrison, "Sequentially derived mutants of the constant region of the heavy chain of murine immunoglobulins," *J Immun*, 1979, 123:793-800.

Morrison, "Transfer and Expression of Immunoglobulin Genes," *Annu Rev Immunol*, 1984, 2:239-256.

Morrison, "Transfectomas Provide Novel Chimeric Antibodies," *Science*, 1985, 229:1202-1207.

Morrison and Oi, "Genetically engineered antibody molecules," *Adv Immunol*, 1989, 44:65-92.

Mosmann and Coffman, "TH1 and TH2 Cells: Different Patterns of Lymphokine Secretion Lead to Different Functional Properties," *Ann Rev Immunol*, 1989, 7:145-173.

Nagy et al., "Fully human, HLA-DR-specific monoclonal antibodies efficiently induce programmed death of malignant lymphoid cells," *Nat Med*, 2002, 8:801-805.

Newman et al., ""Primatization" of Recombinant Antibodies for Immunotherapy of Human Diseases: A Macaque/Human Chimeric Antibody Against Human CD4," *Biotechnol*, 1992, 10:1455-1460.

Nocentini et al., "A new member of the tumor necrosis factor/nerve growth factor receptor family inhibits T cell receptor-induced apoptosis," *Proc Natl Acad Sci USA*, 1997, 94:6216-6221.

Novotny and Haber, "Structural invariants of antigen binding: Comparison of immunoglobulin $VL$-$V_H$ and $V_L$-$V_L$ domain dimers," *Proc Natl Acad Sci USA*, 1985, 82:4592-4596.

Orlandi et al., "Cloning immunoglobulin variable domains for expression by the polymerase chain reaction," *Proc Natl Acad Sci USA*, 1989, 86:3833-3837.

Padlan, "A possible procedure for reducing the immunogenicity of antibody variable domains while preserving their ligand-binding properties," *Mol Immunol*, 1991, 28:489-498.

Padlan, "Anatomy of the antibody molecule," *Mol Immunol*, 1994, 31:169-217.

Paliard et al., "Simultaneous production of IL-2, IL-4, and IFN-gamma by activated human $CD4^+$ and $CD8^+$ T cell clones," *J Immunol*, 1988, 141:849-855.

Pantoliano et al., "Conformational Stability, Folding, and Ligand-Binding Affinity of Single-Chain Fv Immunoglobulin Fragments Expressed in *Escherichia coli*," *Biochem*, 1991, 30:10117-10125.

De Pascalis et al., "Grafting of "abbreviated" complementarity-determining regions containing specificity-determining residues essential for ligand contact to engineer a less immunogenic humanized monoclonal antibody," *J. Immunol.*, 2002, 169:3076-3084.

Paul and Seder, "Lymphocyte Responses and Cytokines," *Cell*, 1994, 76:241-251.

Paul, *Fundamental Immunology*, 3rd Edition, 1993, pp. 292-295.

Pedley et al., "The potential for enhanced tumour localization by poly(ethylene glycol) modification of anti-CEA antibody," *Br J Cancer*, 1994, 70:1126-1130.

Presta, "Antibody engineering," *Curr Opin Struct Biol*, 1992, 3(4):394-398.

Queen et al., "A humanized antibody that binds to the interleukin 2 receptor," *Proc Natl Acad Sci USA*, 1989, 86:10029-10033.

Queen et al., "Cell-Type Specific Regulation of a κ Immunoglobulin Gene by Promoter and Enhancer Elements," *Immunol Rev*, 1986, 89:49-68.

Raso and Griffin, "Hybrid Antibodies with Dual Specificity for the Delivery of Ricin to Immunoglobulin-bearing Target Cells," *Cancer Res*, 1981, 41:2073-2078.

R&D Systems, "Monoclonal, Anti-human GITR/TNFRSF18 Antibody," Catalog No. MAB689, 2002.

R&D Systems, "Monoclonal, Anti-mouse GITR/TNFRSF18 Antibody," Catalog No. MAB5241, 2006.

Riechmann et al., "Reshaping human antibodies for therapy," *Nature*, 1988, 332:323-327.

Ronchetti et al., "GITR, a member of the TNF receptor superfamily, is costimulatory to mouse T lymphocyte subpopulations," *Eur J Immnol*, 2004, 34:613-622.

Rossi, "Therapeutic antisense and ribozymes," *Br Med Bull*, 1995, 51:217-225.

Ruberti et al., "The use of the RACE method to clone hybridoma cDNA when V region primers fail," *J Immunol Meth*, 1994, 173:33-39.

Rudikoff et al., "Single amino acid substitution altering antigen-binding specificity," *Proc. Natl. Acad. Sci. USA*, 1982, 79:1979-1983.

Sblattero and Bradbury, "A definitive set of oligonucleotide primers for amplifying human V regions," *Immunotechnol*, 1998, 3:271-278.

Sharp and Zamore, "Molecular biology. RNA interference," *Science*, 2000, 287:2431-2432.

Shields et al., "High resolution mapping of the binding site on human IgG1 for Fc gamma RI, Fc gamma RII, Fc gamma RIII, and FcRn and design of IgG1 variants with improved binding to the Fc gamma R," *J Biol Chem*, 2001, 276:6591-6604.

Shimizu et al., "Stimulation of $CD25^+CD4^+$ regulatory T cells through GITR breaks immunological self-tolerance," *Nat Immunol*, 2002, 3(2):135-142.

Stahli et al., "Distinction of Epitopes by Monoclonal Antibodies," *Meth Enzymol*, 1983, 92:242-253.

Stephens et al., "Engagement of Glucocorticoid-Induced TNFR Family-Related Receptor on Effector T Cells by its Ligand Mediates Resistance to Suppression by $CD4^+CD25^+$ T Cells," *J Immunol*, 2004, 173:5008-5020.

Strejan et al., "Suppression of chronic-relapsing experimental allergic encephalomyelitis in strain-13 guinea pigs by administration of liposome-associated myelin basic protein," *J Neuroimmunol*, 1984, 7:27.

Takkinen et al., "An active single-chain antibody containing a cellulose linker domain is secreted by *Escherichia coli*," *Protein Eng*, 1991, 4:837-841.

Tallarida, *Drug Synergism and Dose-effect Analysis*, 2000, Chapman & Hall/CRC, Boca Raton, pp. 1-13.

Taylor et al., "A transgenic mouse that expresses a diversity of human sequence heavy and light chain immunoglobulins," *Nucl Acids Res.*, 1992, 20:6287-6295.

Tempest et al., "Reshaping a human monoclonal antibody to inhibit human respiratory syncytial virus infection in vivo," *Biotechnol*, 1991, 9:266-271.

Thompson et al., "Affinity maturation of a high-affinity human monoclonal antibody against the third hypervariable loop of human immunodeficiency virus: use of phage display to improve affinity and broaden strain reactivity," *J Mol Biol*, 1996, 256:77-88.

Tone et al., "Mouse Glucocorticoid-induced tuor necrosis factor receptor Ligand is costimulatory for T cells," *Proc Natl Acad Sci USA*, 2003, 100(25):15059-15064.

Tramontano et al., "Framework Residue 71 is a Major Determinant of the Position and Conformation of the Second Hypervariable Region in the $V_H$ Domains of Immunoglobulins," *J Mol Biol*, 1990, 215:175-182.

Tuschl et al., "Targeted mRNA degradation by double-stranded RNA in vitro," *Genes Dev*, 1999, 13:3191-3197.

Urlaub and Chasin, "Isolation of Chinese hamster cell mutants deficient in dihydrofolate reductase activity," *Proc Natl Acad Sci USA*, 1980, 77:4216-4220.

Verhoeyen et al., "Reshaping Human Antibodies: Grafting an Antilysozyme Activity," *Science*, 1988, 239:1534-1536.

Wagner, "Gene inhibition using antisense oligodeoxynucleotides," *Nature*, 1994, 372:333-335.

Waldmann and Cobbold, "Regulating the Immune Response to Transplants: A Role for $CD4^+$ Regulatory Cells?" *Immunity*, 2001, 14:399-408.

Wilson et al., "The use of mRNA display to select high-affinity protein-binding peptides," *Proc Natl Acad Sci USA*, 2001, 98(7):3750-3755.

Winter and Milstein, "Man-made antibodies," *Nature*, 1991, 349:293-299.

Winter et al., "Making antibodies by phage display technology," *Annu Rev Immunol*, 1994, 12:433-455.

(56) References Cited

OTHER PUBLICATIONS

Yang et al., "Identification of the Ebola virus glycoprotein as the main viral determinant of vascular cell cytotoxicity and injury," *Nat Med*, 2000, 6:886-889.

Zamore et al., "RNAi: double-stranded RNA directs the ATP-dependent cleavage of mRNA at 21 to 23 nucleotide intervals," *Cell*, 2000, 101:25-33.

Zapata et al., *FASEB J*, 1995, 9:A1479.

International Preliminary Report on Patentability for Application No. PCT/US2006/011114, dated Sep. 25, 2007.

Authorized officer Dorothée Mülhausen, International Preliminary Report on Patentability in PCT/US2008/008502, dated Jan. 21, 2010, 9 pages.

Abraham et al., Pharmacogenetics of cancer chemotherapy, BBA Rev Cancer, Elsevier Sci BV, 1766(2):168-183, Dec. 2006.

A. D. Cohen et al., Agonist Anti-GITR Antibody Enhances Vaccine-Induced CD8+ T-Cell Responses and Tumor Immunity, Cancer Res, 66(9):4904-4912, May 2006.

A.D. Cohen et al., An agonist anti-GITR antibody enhances effector and memory CD8 T cell responses and tumor immunity following xenogeneic DNA immunization against melanoma, Proc Amer Assoc Cancer Res, 46:624, Apr. 2005.

Gaffney et al., DNA vaccination targeting mesothelin combined with anti-GITR antibody induces rejection of pancreatic adenocarcinoma, Proc Amer Assoc Cancer Res, 47, Apr. 2006 p. 329.

Montagut et al., Glucocorticoid-induced TNF receptor family related gene activation overcomes tolerance/ignorance to melanoma differentiation antigens and enhances antitumor immunity, J Immunol, 176(11):6434-6442, Jun. 2006.

Extended European Search Report for Intl Application No. PCT/US2008008502, dated Jan. 30, 2013.

Turk et al., "Concomitant tumor immunity to a poorly immunogenic melanoma is prevented by regulatory T cells", J. Exper. Med., 200(6):771-782 (Sep. 20, 2004).

European Search Report, dated May 31, 2011, EP App. No. 10181638.7.

The Merck Manual, 18$^{th}$ edition, Japanese version, Nikkei BP, Apr. 25, 2007, pp. 1227-1230.

* cited by examiner

COMBINATION THERAPIES EMPLOYING GITR BINDING MOLECULES

RELATED APPLICATIONS

This application claims priority to U.S. Provisional Application, 60/959,246, filed on Jul. 12, 2007, titled "Combination Therapies Employing GITR Binding Molecules", 61/001,021, filed on Oct. 30, 2007, titled "Combination Therapies Employing GITR Binding Molecules", and U.S. Ser. No. 61/126,431, filed on May 5, 2008, titled "Combination Therapies Employing GITR Binding Molecules", the entire contents of each are hereby incorporated by reference.

BACKGROUND OF THE INVENTION

Cancer is one of the most prevalent health problems in the world today, affecting approximately one in five individuals in the United States. A variety of chemotherapeutic agents are routinely employed to combat cancer. Unfortunately, many of these drugs have some toxicity at the doses which are effective against tumors. In addition, chemotherapy resistance is a major cause of cancer treatment failure. Strategies for improving cancer treatment have been developed over the years, but there is still a need for effective therapies. Methods of enhancing the anti-tumor effects of chemotherapeutics would be useful for treating or reducing the advancement, severity or effects of neoplasia in subjects (e.g., humans).

SUMMARY OF THE INVENTION

The present invention is based, at least in part, on the discovery that combination therapies employing a GITR binding molecule, e.g., an anti-GITR antibody, and at least one additional agent, which is not a GITR binding molecule, (e.g., a chemotherapeutic agent) are more effective at treating and/or preventing cancer and/or reducing the size of certain tumors than the administration of an agent or agents without a GITR binding molecule. Moreover, in one embodiment, a combination therapy of the invention has an improved safety profile. For example, in one embodiment, because the combination therapy of the invention is more effective, at least one of the agents may be used at a dose lower than that required for efficacy when used alone.

Accordingly, in one aspect the present invention provides a method for inhibiting tumor cell growth in a subject, comprising administering a GITR binding molecule, or an antigen-binding fragment thereof, and one or more cycles of at least one additional agent to the subject, such that tumor cell growth is inhibited in the subject.

In another aspect, the invention provides a method for reducing tumor size in a subject having a tumor, comprising administering a GITR binding molecule, or an antigen-binding fragment thereof, and one or more cycles of at least one additional agent to the subject, such that the tumor size is reduced.

In one embodiment, the at least one additional agent is administered to the subject prior to administration of the GITR binding molecule, or antigen-binding fragment thereof. In another embodiment, the at least one additional agent is administered to the subject concomitantly with the GITR binding molecule, or antigen-binding fragment thereof. In yet another embodiment, the at least one additional agent is administered to the subject following administration of the GITR binding molecule, or antigen-binding fragment thereof.

In one embodiment, the at least one additional agent is a chemotherapeutic agent. In one embodiment, the chemotherapeutic agent is an antimetabolite. In one embodiment, the antimetabolite is selected from the group consisting of Aminopterin, Methotrexate, Pemetrexed, Raltitrexed, Cladribine, Clofarabine, Fludarabine, Mercaptopurine, Pentostatin, Thioguanine, Capecitabine, Cytarabine, Fluorouracil, Floxuridine, and Gemcitabine. In one embodiment, the antimetabolite is a nucleoside analogue. In one embodiment, the nucleoside analogue is gemcitabine. In another embodiment, the nucleoside analogue is fluorouracil. In one embodiment, the chemotherapeutic agent is an agent that affects microtubule formation. In one embodiment, the agent that affects microtubule formation is selected from the group consisting of: paclitaxel, docetaxel, vincristine, vinblastine, vindesine, vinorelbin, taxotere, etoposide, and teniposide. In another embodiment, the agent that affects microtubule formation is paclitaxel. In one embodiment, the chemotherapeutic agent is an alkylating agent. In one embodiment, the alkylating agent is cyclophosphamide. In one embodiment, the chemotherapeutic agent is a cytotoxic antibiotic. In one embodiment, the cytotoxic antibiotic is a topoisomerase II inhibitor. In one embodiment, the topoisomerase II inhibitor is doxorubicin.

In one embodiment, the GITR binding molecule is a humanized antibody or antibody fragment thereof. In one embodiment, the GITR binding molecule is a human antibody or antibody fragment thereof. In one embodiment, the humanized antibody comprises the CDRs shown in SEQ ID NOs.:1, 2 or 3, 4, 5, 6, or 7. In another embodiment, the GITR binding molecule is a chimeric antibody or antibody fragment thereof.

In one embodiment, the type of tumor is selected from the group consisting of: pancreatic cancer, melanoma, breast cancer, lung cancer, bronchial cancer, colorectal cancer, prostate cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, and cancer of hematological tissues. In one embodiment, the tumor is a colon tumor. In one embodiment, the colon tumor is an adenocarcinoma. In another embodiment, the tumor is selected from the group consisting of a colon tumor, a lung tumor, a breast tumor, a stomach tumor, a prostate tumor, a cervical tumor, a vaginal tumor, and a pancreatic tumor. In yet another embodiment, the tumor is at a stage selected from the group consisting of Stage I, Stage II, Stage III, and Stage IV.

In one embodiment, the tumor is at least about 0.5 mm×0.5 mm. In another embodiment, the tumor is at least about 1 mm×1 mm. In yet another embodiment, the tumor has a volume of at least about 100 $mm^3$.

In one embodiment, the tumor is metastatic.

In one embodiment, the administration of a GITR binding molecule, or an antigen-binding fragment thereof, and at least one chemotherapeutic agent results in an inhibition of tumor size by at least about 42% to at least about 90%.

In another aspect, the invention provides a method for reducing tumor size in a subject having adenocarcinoma of the colon comprising administering an anti-GITR antibody, or an antigen-binding fragment thereof, and one or more cycles of gemcitabine to the subject, such that the tumor size is reduced.

In one embodiment, the tumor is an established tumor at the initiation of treatment.

In another aspect, the invention provides a method for reducing tumor size in a subject having melanoma comprising administering a GITR antibody, or an antigen-binding fragment thereof, and one or more cycles of paclitaxel to the subject, such that the tumor size is reduced.

In one embodiment, the tumor is an established tumor at the initiation of treatment. In another embodiment, the tumor is a secondary tumor at the initiation of treatment.

In yet another aspect, the invention provides a method for reducing tumor size in a subject having adenocarcinoma of the colon comprising administering a GITR antibody, or an antigen-binding fragment thereof, and one or more cycles of cyclophosphamide to the subject, such that the tumor size is reduced.

In one embodiment, the tumor is an established tumor at the initiation of treatment. In another embodiment, the tumor is a secondary tumor at the initiation of treatment.

In another aspect, the invention provides a method for reducing tumor size in a subject having adenocarcinoma of the colon comprising administering a GITR antibody, or an antigen-binding fragment thereof, and one or more cycles of fluorouracil to the subject, such that the tumor size is reduced.

In one embodiment, the tumor is an established tumor at the initiation of treatment. In another embodiment, the tumor is a secondary tumor at the initiation of treatment.

In another aspect, the invention provides a method for reducing tumor size in a subject having adenocarcinoma of the colon comprising administering a GITR antibody, or an antigen-binding fragment thereof, and one or more cycles of doxorubicin to the subject, such that the tumor size is reduced.

In one embodiment, the tumor is an established tumor at the initiation of treatment. In another embodiment, the tumor is a secondary tumor at the initiation of treatment.

In one embodiment, the anti-GITR antibody is a humanized antibody or antibody fragment thereof. In one embodiment, the humanized antibody comprises the CDRs shown in SEQ ID NOs.:1, 2 or 3, 4, 5, 6, or 7. In another embodiment, the GITR binding molecule is a chimeric antibody or antibody fragment thereof.

Yet another aspect of the invention provides a kit comprising: a) a packaging material; b) a GITR binding molecule, or antigen-binding fragment thereof, and c) a label or package insert contained within the packaging material indicating that the GITR binding molecule, or antigen-binding fragment thereof, can be administered with at least one additional agent.

In one embodiment, the at least one additional agent is a chemotherapeutic agent. In one embodiment, the chemotherapeutic agent is an antimetabolite. In one embodiment, the antimetabolite is a nucleoside analogue. In one embodiment, the nucleoside inhibitor is gemcitabine. In another embodiment, the nucleoside analogue is fluorouracil. In one embodiment, the chemotherapeutic agent is an agent that affects microtubule formation. In one embodiment, the agent that affects microtubule formation is selected from the group consisting of: paclitaxel, docetaxel, vincristine, vinblastine, vindesine, vinorelbin, taxotere, etoposide, and teniposide. In another embodiment, the agent that affects microtubule formation is paclitaxel. In one embodiment, the chemotherapeutic agent is an alkylating agent. In one embodiment, the alkylating agent is cyclophosphamide. In one embodiment, the chemotherapeutic agent is a cytotoxic antibiotic. In one embodiment, the cytotoxic antibiotic is a topoisomerase II inhibitor. In one embodiment, the topoisomerase II inhibitor is doxorubicin.

In one embodiment, the GITR binding molecule is a humanized antibody or antibody fragment thereof. In one embodiment, the humanized antibody comprises the CDRs shown in SEQ ID NOs.:1, 2 or 3, 4, 5, 6, or 7. In another embodiment, the GITR binding molecule is a chimeric antibody or antibody fragment thereof.

DETAILED DESCRIPTION OF THE INVENTION

Figure 1:
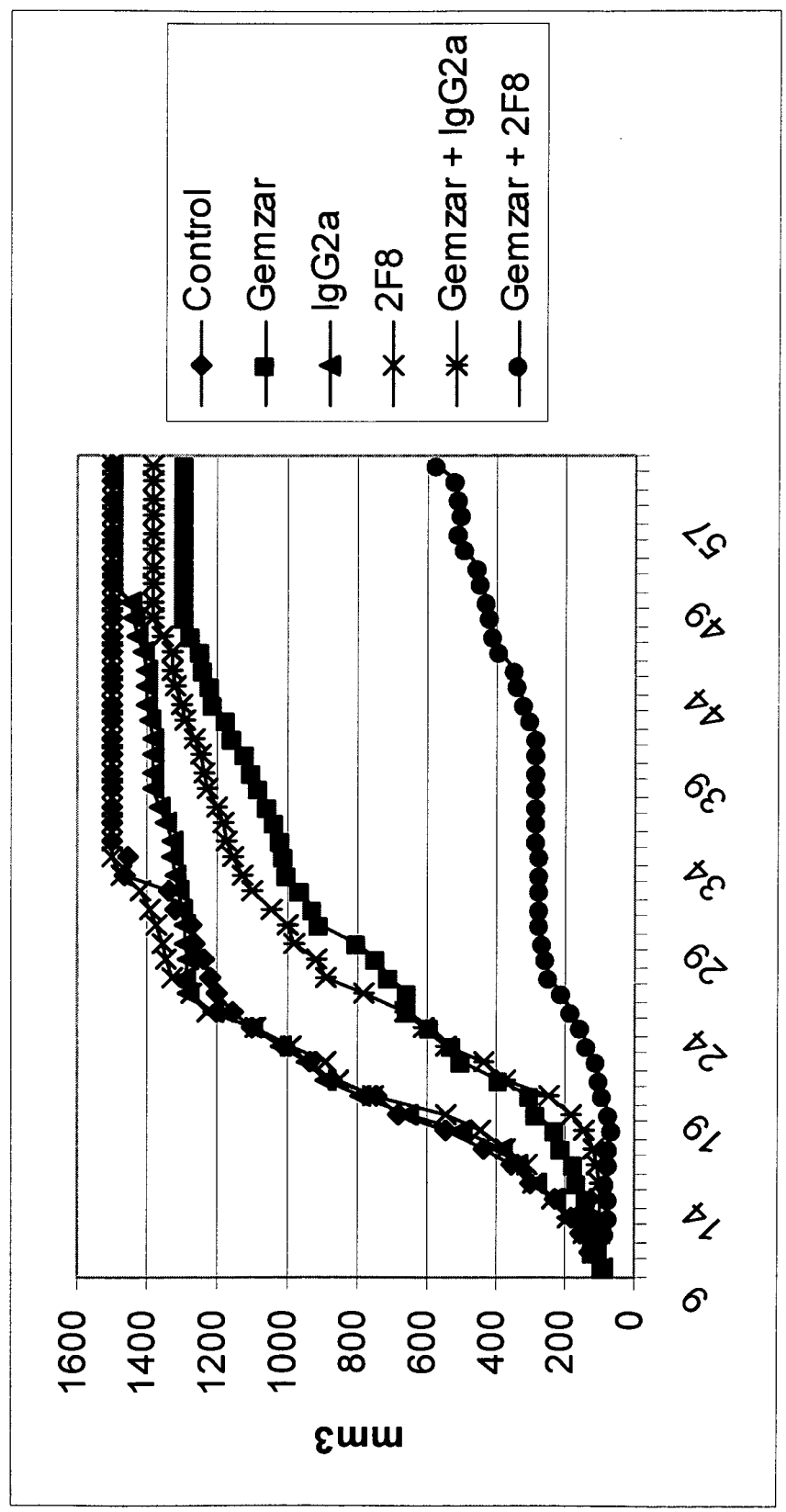
FIG. 1 depicts a graph showing the effect of the nucleoside analog, gemcitabine (Gemzar) (80 mg/kg), in combination with the anti-GITR antibody, 2F8 (0.4 mg), on tumor volume over the course of treatment as compared to the effect of gemcitabine alone, 2F8 alone, and a vehicle control.

The present invention provides, in part, methods and kits for the treatment of cancer. More specifically, it has been shown that combination therapy employing an GITR binding molecule, e.g., an anti-GITR antibody, and at least one additional agent, which is not a GITR binding molecule, (e.g., a chemotherapeutic agent) is more effective at reducing the size of certain tumors than either agent alone.

Glucocorticoid-induced tumor necrosis factor (TNF) receptor family-related gene (GITR), also known as TNF receptor superfamily member 18 (TNFRSF18), is a type I transmembrane protein with homology to TNF receptor family members (Nocentini G, et al. (1997) *Proc Natl Acad Sci*

USA 94:6216-21; Gurney A L, et al. (1999) *Curr Biol* 9:215-8). GITR is expressed at low levels on resting CD4+ and CD8+ T cells and up-regulated following T-cell activation. Ligation of GITR provides a costimulatory signal that enhances both CD4+ and CD8+ T-cell proliferation and effector functions, (Kohm A P, et al. (2004) *J Immunol* 172:4686-90; Kanamaru F, et al. (2004) *J Immunol* 172:7306-14; Ronchetti S, et al. (2004) *Eur J Immunol* 34:613-22; Tone M, et al. (2003) *Proc Natl Acad Sci USA* 100:15059-64; Stephens G L, et al (2004) *J Immunol* 2004; 173:5008-20). In addition, GITR is expressed constitutively at high levels on regulatory T cells. Although GITR has previously been shown to enhance immune responses to certain protein antigens, it has not previously been shown to enhance the anti-tumor effects of agents used to combat cancer.

In order that the present invention may be more readily understood, certain terms are first defined.

I. DEFINITIONS

For convenience, before further description of the present invention, certain terms employed in the specification, examples and appended claims are defined here.

The singular forms "a", "an", and "the" include plural references unless the context clearly dictates otherwise.

The term "administering" includes any method of delivery of a pharmaceutical composition or therapeutic agent into a subject's system or to a particular region in or on a subject. The phrases "systemic administration," "administered systemically", "peripheral administration", and "administered peripherally" as used herein mean the administration of a compound, drug or other material other than directly into the central nervous system, such that it enters the subject's system and, thus, is subject to metabolism and other like processes, for example, subcutaneous administration. "Parenteral administration" and "administered parenterally" means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

The term "glucocorticoid-induced TNF receptor" (abbreviated herein as "GITR"), also known as TNF receptor superfamily 18 (TNFRSF18), TEASR, and 312C2, as used herein, refers to a member of the tumor necrosis factor/nerve growth factor receptor family. GITR is a 241 amino acid type I transmembrane protein characterized by three cysteine pseudorepeats in the extracellular domain and specifically protects T-cell receptor-induced apoptosis, although it does not protect cells from other apoptotic signals, including Fas triggering, dexamethasone treatment, or UV irradiation (Nocentini, G, et al. (1997) *Proc. Natl. Acad. Sci., USA* 94:6216-622). The nucleic acid and amino acid sequences of human GITR (hGITR), of which there are three splice variants, are known and can be found in, for example GenBank Accession Nos. gi:40354198, gi:23238190, gi:23238193, and gi:23238196.

The term "binding molecule" as used herein includes molecules that contain at least one antigen binding site that specifically binds to its target. For example, in one embodiment, a binding molecule for use in the methods of the invention comprises an immunoglobulin antigen binding site or the portion of a ligand molecule that is responsible for receptor binding.

In one embodiment, the binding molecule comprises at least two binding sites. In one embodiment, the binding molecule comprises two binding sites. In one embodiment, the binding molecules comprise three binding sites. In another embodiment, the binding molecule comprises four binding sites.

The term "GITR binding molecule" refers to a molecule that comprises at least one GITR binding site. Examples of GITR binding molecules which are suitable for use in the methods and kits of the invention include, but are not limited to, binding molecules described in, for example, US20070098719, US20050014224, or WO05007190, each of which is incorporated in its entirety by reference herein, or binding molecules comprising CDRs set forth in one of US20070098719, US20050014224, or WO05007190. In another embodiment, a GITR binding molecule may comprise one or more of the CDRs set forth in SEQ ID NOs.:1, 2 or 3, 4, 5, 6, or 7. [SEQ ID NO.:1 (GFSLSTSGMGVG (Heavy Chain CDR1)), SEQ ID NO.:2 (HIWWDDDKYYNPSLKS (HC CDR2N)), SEQ ID NO.:4 (TRRYFPFAY (HC CDR3)), SEQ ID NO.:5 (KASQNVGTNVA (Light Chain CDR1)), SEQ ID NO.:6 (SASYRYS (LC CDR2)), SEQ ID NO.:7 (QQYNTDPLT (LC CDR3)), and SEQ ID NO:3 (HIWWDDDKYYQPSLKS (HC CDR2Q))]. In one embodiment, a binding molecule comprises 1 CDR. In another embodiment, a binding molecule comprises 2 CDRs. In another embodiment, a binding molecule comprises 3 CDRs. In another embodiment, a binding molecule comprises 4 CDRs. In another embodiment, a binding molecule comprises 5 CDRs. In yet another embodiment, a binding molecule comprises all 6 CDRs. Exemplary GITR binding molecules suitable for use in the methods of the invention also include commercially available GITR binding molecule, such as MAB689, available from R&D Systems.

By "specifically binds" it is meant that the binding molecules exhibit essentially background binding to non-GITR molecules. An isolated binding molecule that specifically binds GITR may, however, have cross-reactivity to GITR molecules from other species.

As used herein, the term binding molecule includes, antibodies (including full length antibodies), monoclonal antibodies (including full-length monoclonal antibodies), polyclonal antibodies, multispecific antibodies (e.g., bispecific antibodies), human, humanized or chimeric antibodies, antibody fragments, e.g., Fab fragments, F(ab') fragments, fragments produced by a Fab expression library, epitope-binding fragments of any of the above, and engineered forms of antibodies (i.e., molecules comprising binding sites derived from antibody molecules), e.g., scFv molecules or molecules comprising scFv molecule, so long as they exhibit the desired activity, e.g., binding to GITR. In one embodiment, the GITR binding molecules for use in the combination therapies of the invention bind to GITR on T cells and dendritic cells. In one embodiment, the GITR binding molecules for use in the combination therapies of the invention are characterized by one or more of: binding to hGITR with high affinity, agonizing GITR activity (e.g., in the presence of a stimulating agent, e.g., CD3), and increasing humoral and/or T cell effector responses.

In one embodiment, the binding molecules of the invention are "antibody" or "immunoglobulin" molecules, e.g., naturally occurring antibody or immunoglobulin molecules or genetically engineered antibody molecules that bind antigen in a manner similar to antibody molecules. As used herein, the term "immunoglobulin" includes a polypeptide having a combination of two heavy and two light chains whether or not it possesses any relevant specific immunoreactivity. "Antibodies" refers to such assemblies which have significant known specific immunoreactive activity to an antigen. Antibodies and immunoglobulins comprise light and heavy chains, with or without an interchain covalent linkage between them. Basic immunoglobulin structures in vertebrate systems are relatively well understood.

The generic term "immunoglobulin" comprises five distinct classes of antibody that can be distinguished biochemically. All five classes of antibodies are clearly within the scope of the present invention. With regard to IgG, immunoglobulins comprise two identical light polypeptide chains of molecular weight approximately 23,000 Daltons, and two identical heavy chains of molecular weight 53,000-70,000. The four chains are joined by disulfide bonds in a "Y" configuration wherein the light chains bracket the heavy chains starting at the mouth of the "Y" and continuing through the variable region.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminus is a variable region and at the C-terminus is a constant region; the CH3 and CL domains actually comprise the carboxy-terminus of the heavy and light chain, respectively.

Light chains are classified as either kappa or lambda ($\kappa, \lambda$). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma, mu, alpha, delta, or epsilon, ($\gamma, \mu, \alpha, \delta, \epsilon$) with some subclasses among them (e.g., $\gamma1$-$\gamma 4$). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgA_1$, etc. are well characterized and are known to confer functional specialization. Modified versions of each of these classes and isotypes are readily discernable to the skilled artisan in view of the instant disclosure and, accordingly, are within the scope of the instant invention.

The variable region allows the antibody to selectively recognize and specifically bind epitopes on antigens. That is, the $V_L$ domain and $V_H$ domain of an antibody combine to form the variable region that defines a three dimensional antigen binding site. This quaternary antibody structure forms the antigen binding site present at the end of each arm of the Y. More specifically, the antigen binding site is defined by three complementary determining regions (CDRs) on each of the $V_H$ and $V_L$ chains.

The term "antibody", as used herein, includes whole antibodies, e.g., of any isotype (IgG, IgA, IgM, IgE, etc.), and includes antigen binding fragments thereof. Exemplary antibodies include monoclonal antibodies, polyclonal antibodies, chimeric antibodies, humanized antibodies, human antibodies, and multivalent antibodies. Antibodies may be fragmented using conventional techniques. Thus, the term antibody includes segments of proteolytically-cleaved or recombinantly-prepared portions of an antibody molecule that are capable of actively binding to a certain antigen. Non-limiting examples of proteolytic and/or recombinant antigen binding fragments include Fab, F(ab')2, Fab', Fv, and single chain antibodies (sFv) containing a V[L] and/or V[H] domain joined by a peptide linker.

The binding molecules of the invention may comprise an immunoglobulin heavy chain of any isotype (e.g., IgG, IgE, IgM, IgD, IgA, and IgY), class (e.g., IgG1, IgG2, IgG3, IgG4, IgA1 and IgA2) or subclass of immunoglobulin molecule. Binding molecules may have both a heavy and a light chain.

An "antigen" is an entity (e.g., a proteinaceous entity or peptide) to which a binding molecule specifically binds.

The term "epitope" or "antigenic determinant" refers to a site on an antigen to which a binding molecule specifically binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include, for example, X-ray crystallography and 2-dimensional nuclear magnetic resonance. See, e.g., *Epitope Mapping Protocols in Methods in Molecular Biology*, Vol. 66, G. E. Morris, Ed. (1996).

Binding molecules that recognize the same epitope can be identified in a simple immunoassay showing the ability of one antibody to block the binding of another antibody to a target antigen, i.e., a competitive binding assay. Competitive binding is determined in an assay in which the binding molecule being tested inhibits specific binding of a reference binding molecule to a common antigen, such as GITR. Numerous types of competitive binding assays are known, for example: solid phase direct or indirect radioimmunoassay (RIA); solid phase direct or indirect enzyme immunoassay (EIA) sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual*, Cold Spring Harbor Press (1988)); solid phase direct label RIA using I-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)). Typically, such an assay involves the use of purified antigen bound to a solid surface or cells bearing either of these, an unlabeled test binding molecule and a labeled reference binding molecule. Competitive inhibition is measured by determining the amount of label bound to the solid surface or cells in the presence of the test binding molecule. Usually the test binding molecule is present in excess. Usually, when a competing binding molecule is present in excess, it will inhibit specific binding of a reference binding molecule to a common antigen by at least 50-55%, 55-60%, 60-65%, 65-70% 70-75% or more.

An epitope is also recognized by immunologic cells, for example, B cells and/or T cells. Cellular recognition of an epitope can be determined by in vitro assays that measure antigen-dependent proliferation, as determined by $^3$H-thymidine incorporation, by cytokine secretion, by antibody secretion, or by antigen-dependent killing (cytotoxic T lymphocyte assay).

The term "monoclonal binding molecule" as used herein refers to a binding molecule obtained from a population of substantially homogeneous binding molecules. Monoclonal binding molecules are highly specific, being directed against a single antigenic site. Furthermore, in contrast to polyclonal binding molecule preparations which typically include different binding molecules directed against different determinants (epitopes), each monoclonal binding molecule is directed against a single determinant on the antigen. The modifier "monoclonal" indicates the character of the binding molecule as being obtained from a substantially homogeneous population of binding molecules, and is not to be construed as requiring production of the binding molecule by any particular method. For example, the monoclonal binding molecules to be used in accordance with the present invention may be made by the hybridoma method first described by Kohler, et al., *Nature* 256:495 (1975), or may be made by recombinant DNA methods (see, e.g., U.S. Pat. No. 4,816,567). The "monoclonal binding molecules" may also be isolated from phage antibody libraries using the techniques described in Clackson, et al., *Nature* 352:624-628 (1991) and Marks et al., *J. Mol. Biol.* 222:581-597 (1991), for example.

The term "chimeric binding molecule" refers to a binding molecule comprising amino acid sequences derived from different species. Chimeric binding molecules can be constructed, for example by genetic engineering, from binding molecule gene segments belonging to different species.

The monoclonal binding molecules herein specifically include "chimeric" binding molecules in which a portion of the heavy and/or light chain is identical with or homologous to corresponding sequences in binding molecules derived from a particular species or belonging to a particular antibody class or subclass, while the remainder of the chain(s) is identical with or homologous to corresponding sequences in binding molecules derived from another species or belonging to another antibody class or subclass, as well as fragments of such binding molecules, so long as they exhibit the desired biological activity (U.S. Pat. No. 4,816,567; and Morrison, et al., *Proc. Natl. Acad. Sci. USA* 81:6851-6855 (1984)) e.g., binding to GITR, e.g., human GITR (hGITR) and increasing T effector and/or humoral responses.

"Humanized" forms of non-human (e.g., murine) binding molecules are antibodies which contain minimal sequence derived from non-human binding molecule. For the most part, humanized binding molecules are human binding molecules (acceptor/recipient binding molecule) in which the CDR residues from the hyper-variable region are replaced by CDR residues from a hypervariable region of a non-human species (donor binding molecule) such as mouse, rat, rabbit or non-human primate having the desired specificity, affinity, and capacity. In some instances, Fv framework region (FR) residues of the human binding molecule are altered, e.g., replaced by or substituted with non-donor residues (e.g., germline residues), or backmutated to corresponding donor human residues. Furthermore, humanized binding molecules may comprise residues which are not found in the recipient binding molecule or in the donor binding molecule. These modifications are generally made to further refine binding molecule performance. In general, the humanized binding molecule will comprise substantially all of at least one, and typically two, variable domains, in which all or substantially all of the hypervariable loops correspond to those of a non-human binding molecule and all or substantially all of the FR regions are those of a human binding molecule sequence. The humanized binding molecule optionally also will comprise at least a portion of a binding molecule constant region (Fc), typically that of a human binding molecule. For further details, see Jones, et al., *Nature* 321:522-525 (1986); Riechmann, et al., *Nature* 332:323-329 (1988); and Presta, *Curr. Op. Struct. Biol.* 2:593-596 (1992).

The term "multispecific" includes binding molecules having specificity for more than one target antigen. Such molecules have more than one binding site where each binding site specifically binds (e.g., immunoreacts with) a different target molecule or a different antigenic site on the same target.

In one embodiment, a multispecific binding molecule of the invention is a bispecific molecule (e.g., antibody, minibody, domain deleted antibody, or fusion protein) having binding specificity for at least two targets, e.g., more than one target molecule or more than one epitope on the same target molecule.

In one embodiment, modified forms of antibodies can be made from a whole precursor or parent antibody using techniques known in the art. Exemplary techniques are discussed in more detail below. In particularly preferred embodiments both the variable and constant regions of polypeptides of the invention are human. In one embodiment, fully human antibodies can be made using techniques that are known in the art. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make antibodies are described in U.S. Pat. Nos. 6,150,584; 6,458,592; 6,420,140. Other techniques, such as the use of libraries, are known in the art.

In one embodiment, a binding molecule of the invention comprises an antibody molecule, e.g., an intact antibody molecule, or a fragment of an antibody molecule. In another embodiment, a binding molecule of the invention is a modified or synthetic antibody molecule. In one embodiment, a binding molecule of the invention comprises all or a portion of (e.g., at least one antigen binding site from, at least one CDR from) a monoclonal antibody, a humanized antibody, a chimeric antibody, or a recombinantly produced antibody.

In embodiments where the binding molecule is an antibody or modified antibody, the antigen binding site and the heavy chain portions need not be derived from the same immunoglobulin molecule. In this regard, the variable region may be derived from any type of animal that can be induced to mount a humoral response and generate immunoglobulins against the desired antigen. As such, the variable region of the polypeptides may be, for example, of mammalian origin e.g., may be human, murine, rat, non-human primate (such as cynomolgus monkeys, macaques, etc.), lupine, camelid (e.g., from camels, llamas and related species). In another embodiment, the variable region may be condricthoid in origin (e.g., from sharks).

In one embodiment, the binding molecules of the invention are modified antibodies. As used herein, the term "engineered" or "modified antibody" includes synthetic forms of antibodies which are altered such that they are not naturally occurring, e.g., antibodies that do not comprise complete heavy chains (such as, domain deleted antibodies or minibodies); multispecific forms of antibodies (e.g., bispecific, trispecific, etc.) altered to bind to two or more different antigens or to different epitopes on a single antigen); heavy chain molecules joined to scFv molecules and the like. ScFv molecules are known in the art and are described, e.g., in U.S. Pat. No. 5,892,019. In addition, the term "engineered" or "modified antibody" includes multivalent forms of antibodies (e.g., trivalent, tetravalent, etc., antibodies that bind to three or more copies of the same antigen or different antigens or different epitopes on the same antigen).

In one embodiment, the term, "modified antibody" according to the present invention includes immunoglobulins, antibodies, or immunoreactive fragments or recombinant forms thereof, in which at least a fraction of one or more of the constant region domains has been deleted or otherwise altered (e.g., mutated) so as to provide desired biochemical characteristics such as the ability to non-covalently dimerize, increased ability to localize at the site of a tumor, or altered serum half-life when compared with a whole, unaltered antibody of approximately the same immunogenicity.

In one embodiment, the binding molecules of the invention may be modified to reduce their immunogenicity using art-recognized techniques. For example, antibodies or polypeptides of the invention can be humanized, deimmunized, or chimeric antibodies can be made. These types of antibodies are derived from a non-human antibody, typically a murine antibody, that retains or substantially retains the antigen-binding properties of the parent antibody, but which is less immunogenic in humans. This may be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues. Such methods are disclosed in Morrison et al., *Proc. Natl. Acad. Sci.* 81: 6851-5 (1984); Morrison et al., *Adv. Immunol.* 44: 65-92 (1988); Verhoeyen et al., *Science* 239: 1534-1536 (1988); Padlan, *Molec. Immun.* 28: 489-498 (1991); Padlan, *Molec. Immun.* 31: 169-217 (1994), and U.S. Pat. Nos. 5,585,089, 5,693,761 and 5,693,762 all of which are hereby incorporated by reference in their entirety.

The term "chemotherapeutic agent", used interchangeably herein with "chemotherapy agent" and "antineoplastic agent", refers to a substance that inhibits or prevents the viability and/or function of cells, and/or causes destruction of cells (cell death), and/or exerts anti-neoplastic/anti-proliferative effects, for example, prevents directly or indirectly the development, maturation or spread of neoplastic tumor cells. The term also includes such agents that cause a cytostatic effect only and not a mere cytotoxic effect. As used herein the term chemotherapeutic agents includes anti-angiogenic agents, tyrosine kinase inhibitors, protein kinase A inhibitors, members of the cytokine family, and radioactive isotopes.

Suitable chemotherapeutic agents according to the invention are preferably natural or synthetic chemical compounds. There are large numbers of anti-neoplastic chemical agents available in commercial use, in clinical evaluation and in pre-clinical development, which may be used in the combination therapies of the invention (discussed below).

The term "biologic" or "biologic agent" refers to any pharmaceutically active agent made from living organisms and/or their products which is intended for use as a therapeutic, e.g., toxins such as enzymatically active toxins of bacterial, fungal, plant or animal origin. In one embodiment of the invention, biologic agents which can be used in combination with a GITR binding molecule include, but are not limited to e.g., antibodies, nucleic acid molecules, e.g., antisense nucleic acid molecules, polypeptides or proteins. Such biologics can be administered in combination with a GITR binding molecule by administration of the biologic agent, e.g., prior to the administration of the GITR binding molecule, concomitantly with the GITR binding molecule, or after the GITR binding molecule.

The term "combination therapy", as used herein, refers to a therapeutic regimen comprising, e.g., a GITR binding molecule and at least one additional non-GITR binding molecule, e.g., a chemotherapeutic agent. The GITR binding molecule and the at least one additional agent may be formulated for separate administration or may be formulated for administration together. In one embodiment, the at least one additional agent is not a molecule to which an immune response is desired, e.g., is not a vaccine.

The term "cancer" or "neoplasia" refers in general to a malignant neoplasm or spontaneous growth or proliferation of cells. Cancer cells are often in the form of a tumor, but such cells may exist alone within a subject, or may be non-tumorigenic cancer cells, such as leukemia cells. As used herein, the term "cancer" includes pre-malignant as well as malignant cancers.

A subject having "cancer", for example, may have a leukemia, lymphoma, or other malignancy of blood cells. In one embodiment, cancer is selected from the group consisting of pancreatic cancer, melanoma and other forms of skin cancer (e.g., squamous cell carcinoma) breast cancer, lung cancer, bronchial cancer, colorectal cancer, prostate cancer, stomach cancer, ovarian cancer, brain or central nervous system cancer, peripheral nervous system cancer, esophageal cancer, cervical cancer, uterine or endometrial cancer, cancer of the head and neck (including cancer of the oral cavity or nasopharynx), liver and biliary tract cancer, kidney and renal collecting system, including urinary bladder cancer, testicular cancer, small bowel or appendix cancer, salivary gland cancer, thyroid gland cancer, adrenal gland cancer, sarcomas (including osteosarcoma and chondrosarcoma), and cancer of hematological tissues.

In certain embodiments, the subject methods are used to treat a solid tumor. Exemplary solid tumors include but are not limited to small and non-small cell lung cancer (NSCLC), testicular cancer, ovarian cancer, uterine cancer, cervical cancer, pancreatic cancer, colorectal cancer (CRC), breast cancer, as well as prostate, gastric, skin, stomach, esophageal, and bladder cancer.

In one embodiment, a solid tumor is an adenocarcinoma, e.g., of the colon. In one embodiment of the invention, a solid tumor is a colon tumor. In another embodiment of the invention, a solid tumor is selected from the group consisting of a colon tumor, a lung tumor, a breast tumor, a stomach tumor, a prostate tumor, a cervical tumor, a vaginal tumor, and a pancreatic tumor.

In one embodiment of the invention, the cancer to be treated is a melanoma.

In certain embodiments of the invention, the subject methods are used to reduce and/or prevent tumor cell proliferation. In certain embodiments of the invention, the subject methods are used to reduce and/or prevent tumor metastasis. In another embodiment, the subject methods are used to reduce the size of a tumor, e.g., an established tumor, and/or a secondary tumor, e.g., a metastasis. As used herein, an "established tumor" is a solid tumor of sufficient size such that nutrients, i.e., oxygen can no longer permeate to the center of the tumor from the subject's vasculature by osmosis and, therefore, the tumor requires its own vascular supply to receive nutrients.

In one embodiment, the subject methods are used to treat a vascularized tumor. The term "vascularized tumor" includes tumors having the hallmarks of established vasculature. Such tumors are identified by their size and/or by the presence of markers associated with blood vessels or angiogenesis. In one embodiment, the tumor is at least about 0.5 mm×0.5 mm. In another embodiment, the tumor is at least about 1 mm×1 mm. In yet another embodiment, the tumor has a volume of at least about 100 mm$^3$. In another embodiment, the tumor has a volume of at least about 200 mm$^3$. In another embodiment, the tumor has a volume of at least about 300 mm$^3$. In another embodiment, the tumor has a volume of at least about 400 mm$^3$. In another embodiment, the tumor has a volume of at least about 500 mm$^3$. In one embodiment, the tumor is large enough to be found by palpation or by using art recognized imaging techniques.

In another embodiment, the subject methods are used to treat a solid tumor that is not quiescent and is actively undergoing exponential growth. In another embodiment, the subject methods are used to treat a small tumor, such as a micrometastasis, e.g., a tumor detectable only by histological examination but not by other techniques.

The term "effective amount" refers to that amount of combination therapy which is sufficient to produce a desired result on a cancerous cell or tumor, including, but not limited to, for example, reducing tumor size and/or reducing tumor volume of a solid tumor, either in vitro or in vivo. In one embodiment of the invention, an effective amount of a combination therapy is the amount that results in an inhibition of tumor size more than about 10%, more than about 20%, more than about 30%, more than about 35%, more than about 42%, more than about 43%, more than about 44%, more than about 45%, more than about 46%, more than about 47%, more than about 48%, more than about 49%, more than about 50%, more than about 51%, more than about 52%, more than about 53%, more than about 54%, more than about 55%, more than about 56%, more than about 57%, more than about 58%, more than about 59%, more than about 60%, more than about 65%, more than about 70%, more than about 75%, more than about 80%, more than about 85%, more than about 90%, more than about 95%, or more than about 100%.

The term also includes that amount of a combination therapy which is sufficient to achieve a desired clinical result, including but not limited to, for example, preventing recurrence, ameliorating disease, stabilizing a patient, preventing or delaying the development of metastasis, or preventing or slowing the progression of cancer in a patient. An effective amount of the combination therapy can be determined based on one administration of each of the agents or repeated administration of at lest one of the agents of the therapy. Methods of detection and measurement of the indicators above are known to those of ordinary skill in the art. Such methods include, but are not limited to measuring reduction in tumor burden, reduction of tumor size, reduction of tumor volume, reduction in proliferation of secondary tumors, decreased solid tumor vascularization, alteration in the expression of genes in tumor tissue or adjacent tissue, presence or absence of biomarkers, lymph node involvement, histologic grade, detecting the lack of recurrence of a tumor, a reduced rate of tumor growth, reduced tumor cell metabolism, and/or nuclear grade.

In one embodiment of the invention, tumor burden is determined. "Tumor burden" also referred to as "tumor load", refers to the total amount of tumor material distributed throughout the body. Tumor burden refers to the total number of cancer cells or the total size of tumor(s), throughout the body, including lymph nodes and bone barrow. Tumor burden can be determined by a variety of methods known in the art, such as, e.g. by measuring the dimensions of tumor(s) upon removal from the subject, e.g., using calipers, or while in the body using imaging techniques, e.g., ultrasound, bone scan, computed tomography (CT) or magnetic resonance imaging (MRI) scans.

In one embodiment of the invention, tumor size is determined. The term "tumor size" refers to the total size of the tumor which can be measured as the length and width of a tumor. Tumor size may be determined by a variety of methods known in the art, such as, e.g by measuring the dimensions of tumor(s) upon removal from the subject, e.g., using calipers, or while in the body using imaging techniques, e.g., bone scan, ultrasound, CT or MRI scans.

In one embodiment of the invention, tumor size is determined by determining tumor weight. In one embodiment, tumor weight is determined by measuring the length of the tumor, multiplying it by the square of the width of the tumor, and dividing that sum by 2.

In one embodiment of the invention, tumor size is determined by determining tumor volume. The term "tumor volume" refers to the total size of the tumor, which includes the tumor itself plus affected lymph nodes if applicable. Tumor volume may be determined by a variety of methods known in the art, such as, e.g. by measuring the dimensions of tumor(s) upon removal from the subject, e.g., using calipers, or while in the body using an imaging techniques, e.g., ultrasound, CT or MRI scans, and calculating the volume using equations based on, for example, the z-axis diameter, or on standard shapes such as the sphere, ellipsoid, or cube. In one embodiment, tumor volume (mm$^3$) is calculated for a prolate ellipsoid from 2-dimensional tumor measurements: tumor volume (mm$^3$)=(length×width$^2$ [L×W$^2$])÷2. Assuming unit density, tumor volume is converted to tumor weight (i.e., 1 mm$^3$=1 mg).

The term "vascularization of a solid tumor" refers to the formation of blood vessels in a solid tumor. Tumor vascularization may be determined by a variety of methods known in the art, such as, e.g. by immunohistochemical analysis of biopsy specimens, or by imaging techniques, such as sonography of the tumor, angiography, CT or magnetic MRI scans.

The term "% T/C" is the percentage of the mean tumor weight of the Treatment group (T) divided by the mean tumor weight of the Control group (C) multiplied by 100. A % T/C value of 42% or less is considered indicative of meaningful activity by the National Cancer Institute (USA).

The term "% inhibition" with respect to T/C is calculated by subtracting the % T/C from 100.

The term "statistically significant" or "statistical significance" refers to the likelihood that a result would have occurred by chance, given that an independent variable has no effect, or, that a presumed null hypothesis is true. Statistical significance can be determined by obtaining a "P-value" (P) which refers to the probability value. The p-value indicates how likely it is that the result obtained by the experiment is due to chance alone. In one embodiment of the invention, statistical significance can be determined by obtaining the p-value of the Two-Tailed One-Sample T-Test. A p-value of less than 0.05 is considered statistically significant, that is, not likely to be due to chance alone. Alternatively a statistically significant p-value may be between about 0.05 to about 0.04; between about 0.04 to about 0.03; between about 0.03 to about 0.02; between about 0.02 to about 0.01. Ranges intermediate to the above recited values, e.g., are also intended to be part of this invention. In certain cases, the p-value may be less than 0.01. The p-value may be used to determine whether or not there is any statistically significant reduction in tumor size and/or any statistically significant increase in survival when combination therapy is used to treat a subject having a tumor.

"Treating cancer" or "treating a subject having cancer" includes inhibition of the replication of cancer cells, inhibition of the spread of cancer, reduction in tumor size, lessening or reducing the number of cancerous cells in the body, and/or amelioration or alleviation of the symptoms of cancer. A treatment is considered therapeutic if there is a decrease in mortality and/or morbidity, and may be performed prophylactically, or therapeutically.

A "patient" or "subject" or "host" refers to either a human being or non-human animal.

Various aspects of the invention are described in further detail in the following subsections.

II. GITR BINDING MOLECULES

GITR binding molecules for use in the methods of the invention include binding molecules that specifically bind to GITR and act as a GITR agonist (as demonstrated by, e.g., increased effector T cell response and/or increased humoral immunity), such as, for example, those binding molecules described in US20070098719, US20050014224, and WO05007190.

In one embodiment, the GITR binding molecule is an anti-GITR antibody. Various forms of anti-GITR antibodies can be made using standard recombinant DNA techniques (Winter and Milstein, Nature, 349, pp. 293-99 (1991)).

In certain embodiments, the GITR binding molecule may be a polyclonal antibody. For example, antibodies may be raised in mammals by multiple subcutaneous or intraperitoneal injections of the relevant antigen and an adjuvant. This immunization typically elicits an immune response that comprises production of antigen-reactive antibodies from activated splenocytes or lymphocytes. The resulting antibodies may be harvested from the serum of the animal to provide polyclonal preparations.

Chimeric and/or humanized binding molecules (i.e., chimeric and/or humanized immunoglobulins) specific for GITR are also suitable for use in the methods of the invention. Chimeric and/or humanized binding molecules have the same or similar binding specificity and affinity as a mouse or other nonhuman binding molecules that provide the starting material for construction of a chimeric or humanized binding molecule.

A chimeric binding molecule is one whose light and heavy chain genes have been constructed, typically by genetic engineering, from immunoglobulin gene segments belonging to different species. For example, the variable (V) segments of the genes from a mouse monoclonal binding molecule may be joined to human constant (C) segments, such as IgG1 or IgG4. Human isotype IgG1 is preferred. An exemplary chimeric binding molecule is thus a hybrid protein consisting of the V or antigen-binding domain from a mouse binding molecule and the C or effector domain from a human binding molecule.

In one embodiment, a binding molecule suitable for use in the methods of the invention comprises a humanized variable region of the 6C8 binding molecule. In one embodiment, a binding molecule of the invention comprises at least one humanized 6C8 binding molecule variable region, e.g., a light chain or heavy chain variable region.

As set forth above, the term "humanized binding molecule" refers to a binding molecule comprising at least one chain comprising variable region framework residues derived from a human binding molecule chain (referred to as the acceptor antibody or binding molecule) and at least one complementarity determining region derived from a mouse-binding molecule, (referred to as the donor antibody or binding molecule). Humanized binding molecules can be produced using recombinant DNA technology. See for example, e.g., Hwang, W. Y. K., et al. (2005) *Methods* 36:35; Queen et al., Proc. Natl. Acad. Sci. USA, (1989), 86:10029-10033; Jones et al., Nature, (1986), 321:522-25; Riechmann et al., Nature, (1988), 332:323-27; Verhoeyen et al., Science, (1988), 239:1534-36; Orlandi et al., Proc. Natl. Acad. Sci. USA, (1989), 86:3833-37; U.S. Pat. Nos. 5,225,539; 5,530, 101; 5,585,089; 5,693,761; 5,693,762; 6,180,370, Selick et al., WO 90/07861, and Winter, U.S. Pat. No. 5,225,539 (incorporated by reference in their entirety for all purposes). The constant region(s), if present, are preferably also derived from a human immunoglobulin.

In certain embodiments, the humanized antibody is humanized 6C8 or antibody fragment thereof, as described, including the nucleotide and amino acid sequence thereof, in US20070098719. In one embodiment, the humanized antibody comprises one or more of the CDRs shown in SEQ ID NOs.:1, 2 or 3, 4, 5, 6, or 7. In one embodiment, the humanized antibody comprises CDRs 1, 2 or 3, 4, 5, 6, and 7.

The humanized binding molecules preferably exhibit a specific binding affinity for antigen of at least $10^7$, $10^8$, $10^9$, $10^{10}$, $10^{11}$, or $10^{12}$ M$^{-1}$. Usually the upper limit of binding affinity of the humanized binding molecules for antigen is within a factor of three, four or five of that of the donor immunoglobulin. Often the lower limit of binding affinity is also within a factor of three, four or five of that of donor immunoglobulin. Alternatively, the binding affinity can be compared to that of a humanized binding molecule having no substitutions (e.g., a binding molecule having donor CDRs and acceptor FRs, but no FR substitutions). In such instances, the binding of the optimized binding molecule (with substitutions) is preferably at least two- to three-fold greater, or three- to four-fold greater, than that of the unsubstituted binding molecule. For making comparisons, activity of the various binding molecules can be determined, for example, by BIACORE (i.e., surface plasmon resonance using unlabelled reagents) or competitive binding assays.

In certain embodiments, a GITR binding molecule is a chimeric antibody. In one embodiment, a chimeric antibody of the invention may be a chimeric 6C8 antibody which is described in U.S. Patent Publication No. US20070098719, the contents of which are expressly incorporated herein by reference.

In certain embodiments, a GITR binding molecule is a monoclonal antibody. In one embodiment, a monoclonal antibody of the invention may be a humanized 6C8 antibody which is also described in U.S. Patent Publication No. US20070098719.

In another embodiment, a binding molecule of the invention comprises at least one CDR derived from a murine human GITR binding molecule, e.g., a 6C8 binding molecule. In another embodiment, a binding molecule of the invention comprises at least one CDR (e.g., 1, 2, 3, 4, 5, or 6 CDRs) derived from a rat GITR binding molecule, e.g., a 2F8 binding molecule. As used herein the term "derived from" a designated protein refers to the origin of the polypeptide. In one embodiment, the polypeptide or amino acid sequence which is derived from a particular starting polypeptide is a CDR sequence or sequence related thereto. In another embodiment, the polypeptide or amino acid sequence which is derived from a particular starting polypeptide is a framework (FR) sequence or sequence related thereto. In one embodiment, the amino acid sequence which is derived from a particular starting polypeptide is not contiguous.

For example, in one embodiment, one, two, three, four, five, or six CDRs are derived from a murine 6C8 antibody. In one embodiment, a binding molecule of the invention comprises at least one heavy or light chain CDR of a murine 6C8 antibody. In another embodiment, a binding molecule of the invention comprises at least two CDRs from a murine 6C8 antibody. In another embodiment, a binding molecule of the invention comprises at least three CDRs from a murine 6C8 antibody. In another embodiment, a binding molecule of the invention comprises at least four CDRs from a murine 6C8 antibody. In another embodiment, a binding molecule of the invention comprises at least five CDRs from a murine 6C8 antibody. In another embodiment, a binding molecule of the invention comprises at least six CDRs from a murine 6C8 antibody.

In one embodiment, a binding molecule of the invention comprises a polypeptide or amino acid sequence that is essentially identical to that of a 6C8 antibody, or a portion thereof, e.g., a CDR, wherein the portion consists of at least 3-5 amino acids, of at least 5-10 amino acids, at least 10-20 amino acids, at least 20-30 amino acids, or at least 30-50 amino acids, or which is otherwise identifiable to one of ordinary skill in the art as having its origin in the starting sequence.

In another embodiment, the polypeptide or amino acid sequence which is derived from a particular starting polypeptide or amino acid sequence shares an amino acid sequence identity that is about 80%, 85%, 86%, 87%, 88%, 89%, 90%, 91%, 92%, 93%, 94%, 95%, 96%, 97%, 98%, 99%, with a 6C8 antibody or portion thereof (e.g., a CDR) or which is otherwise identifiable to one of ordinary skill in the art as having its origin in the starting sequence.

It will also be understood by one of ordinary skill in the art that an anti-GITR binding molecule for use in the methods of the invention may be modified such that it varies in amino acid sequence from the molecule from which it was derived. For example, nucleotide or amino acid substitutions leading to conservative substitutions or changes at "non-essential" amino acid residues may be made (e.g., in CDR and/or framework residues) and maintain, increase, or decrease the ability to bind to GITR, e.g., human GITR.

An isolated nucleic acid molecule encoding a non-natural variant of a polypeptide can be created by introducing one or more nucleotide substitutions, additions or deletions into the nucleotide sequence of the binding molecule such that one or more amino acid substitutions, additions or deletions are introduced into the encoded protein. Mutations may be introduced by standard techniques, such as site-directed mutagenesis and PCR-mediated mutagenesis. In one embodiment, conservative amino acid substitutions are made at one or more non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in a binding molecule polypeptide may be replaced with another amino acid residue from the same side chain family. In another embodiment, a string of amino acids can be replaced with a structurally similar string that differs in order and/or composition of side chain family members.

Alternatively, in another embodiment, mutations may be introduced randomly along all or part of the binding molecule coding sequence.

Preferred binding molecules for use in the methods of the invention comprise framework and constant region amino acid sequences derived from a human amino acid sequence. However, binding molecules may comprise framework and/or constant region sequences derived from another mammalian species. For example, a primate framework region (e.g., non-human primate), heavy chain portion, and/or hinge portion may be included in the subject binding molecules. In one embodiment, one or more murine amino acids may be present in the framework region of a binding polypeptide, e.g., a human or non-human primate framework amino acid sequence may comprise one or more amino acid substitutions and/or backmutations in which the corresponding murine amino acid residue is present. Preferred binding molecules of the invention are less immunogenic than the starting 6C8 murine antibody.

The preparation of monoclonal antibodies is a well-known process (Kohler et al., Nature, 256:495 (1975)) in which the relatively short-lived, or mortal, lymphocytes from a mammal which has been injected with antigen are fused with an immortal tumor cell line (e.g. a myeloma cell line), thus, producing hybrid cells or "hybridomas" which are both immortal and capable of producing the genetically coded antibody of the B cell. The resulting hybrids are segregated into single genetic strains by selection, dilution, and regrowth with each individual strain comprising specific genes for the formation of a single antibody. They produce antibodies which are homogeneous against a desired antigen and, in reference to their pure genetic parentage, are termed "monoclonal."

Hybridoma cells thus prepared are seeded and grown in a suitable culture medium that preferably contains one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. Preferably, the binding specificity of the monoclonal antibodies produced by hybridoma cells is determined by immunoprecipitation or by an in vitro assay, such as a radioimmunoassay (RIA) or enzyme-linked immunoabsorbent assay (ELISA). After hybridoma cells are identified that produce antibodies of the desired specificity, affinity and/or activity, the clones may be subcloned by limiting dilution procedures and grown by standard methods (Goding, Monoclonal Antibodies: Principles and Practice, pp 59-103 (Academic Press, 1986)). It will further be appreciated that the monoclonal antibodies secreted by the subclones may be separated from culture medium, ascites fluid or serum by conventional purification procedures such as, for example, protein-A, hydroxylapatite chromatography, gel electrophoresis, dialysis or affinity.

In another embodiment, DNA encoding a desired monoclonal antibody may be readily isolated and sequenced using conventional procedures (e.g., by using oligonucleotide probes that are capable of binding specifically to genes encoding the heavy and light chains of murine antibodies). The isolated and subcloned hybridoma cells serve as a preferred source of such DNA. Once isolated, the DNA may be placed into expression vectors, which are then transfected into prokaryotic or eukaryotic host cells such as E. coli cells, simian COS cells, Chinese Hamster Ovary (CHO) cells or myeloma cells that do not otherwise produce immunoglobulins. More particularly, the isolated DNA (which may be modified as described herein) may be used to clone constant and variable region sequences for the manufacture antibodies as described in Newman et al., U.S. Pat. No. 5,658,570, filed Jan. 25, 1995, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. As will be discussed in more detail below, transformed cells expressing the desired antibody may be grown up in relatively large quantities to provide clinical and commercial supplies of the immunoglobulin.

Those skilled in the art will also appreciate that DNA encoding antibodies or antibody fragments may also be derived from antibody phage libraries, e.g., using pd phage or Fd phagemid technology. Exemplary methods are set forth, for example, in EP 368 684 B1; U.S. Pat. No. 5,969,108, Hoogenboom, H. R. and Chames. 2000. Immunol. Today 21:371; Nagy et al. 2002. Nat. Med. 8:801; Huie et al. 2001. Proc. Natl. Acad. Sci. USA 98:2682; Lui et al. 2002. J. Mol. Biol. 315:1063, each of which is incorporated herein by reference. Several publications (e.g., Marks et al. *Bio/Technology* 10:779-783 (1992)) have described the production of high affinity human antibodies by chain shuffling, as well as combinatorial infection and in vivo recombination as a strategy for constructing large phage libraries. In another embodiment, Ribosomal display can be used to replace bacteriophage as the display platform (see, e.g., Hanes et al. 2000. *Nat. Biotechnol.* 18:1287; Wilson et al. 2001. *Proc. Natl. Acad. Sci. USA* 98:3750; or Irving et al. 2001 *J. Immunol. Methods* 248:31. In yet another embodiment, cell surface libraries can be screened for antibodies (Boder et al. 2000. *Proc. Natl. Acad. Sci. USA* 97:10701; Daugherty et al. 2000 *J. Immunol. Methods* 243:211. Such procedures provide alternatives to traditional hybridoma techniques for the isolation and subsequent cloning of monoclonal antibodies.

Yet other embodiments of the present invention comprise the generation of human or substantially human antibodies in nonhuman animals, such as transgenic animals harboring one or more human immunoglobulin transgenes. Such animals may be used as a source for splenocytes for producing hybridomas, as is described in U.S. Pat. No. 5,569,825, WO00076310, WO00058499 and WO00037504 and incorporated by reference herein.

Yet another highly efficient means for generating recombinant antibodies is disclosed by Newman, Biotechnology, 10: 1455-1460 (1992). Specifically, this technique results in the generation of primatized antibodies that contain monkey variable domains and human constant sequences. This reference is incorporated by reference in its entirety herein. Moreover, this technique is also described in commonly assigned U.S. Pat. Nos. 5,658,570, 5,693,780 and 5,756,096 each of which is incorporated herein by reference.

In another embodiment, lymphocytes can be selected by micromanipulation and the variable genes isolated. For example, peripheral blood mononuclear cells can be isolated from an immunized mammal and cultured for about 7 days in vitro. The cultures can be screened for specific IgGs that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the Vh and Vl genes can be amplified using, e.g., RT-PCR. The VH and VL genes can be cloned into an antibody expression vector and transfected into cells (e.g., eukaryotic or prokaryotic cells) for expression.

Alternatively, antibody-producing cell lines may be selected and cultured using techniques well known to the skilled artisan. Such techniques are described in a variety of laboratory manuals and primary publications. In this respect, techniques suitable for use in the invention as described below are described in Current Protocols in Immunology, Coligan et al., Eds., Green Publishing Associates and Wiley-Interscience, John Wiley and Sons, New York (1991) which is herein incorporated by reference in its entirety, including supplements.

Variable and constant region domains can be obtained from existing sources, (e.g., from one or more of the anti-GITR antibodies described herein) and be incorporated into a modified binding molecule of the invention. For example, to clone antibodies, mRNA can be isolated from hybridoma, spleen, or lymph cells, reverse transcribed into DNA, and antibody genes amplified by PCR. PCR may be initiated by consensus constant region primers or by more specific primers based on the published heavy and light chain DNA and amino acid sequences. PCR also may be used to isolate DNA clones encoding the antibody light and heavy chains. In this case the libraries may be screened by consensus primers or larger homologous probes, such as mouse constant region probes. Numerous primer sets suitable for amplification of antibody genes are known in the art (e.g., 5' primers based on the N-terminal sequence of purified antibodies (Benhar and Pastan. 1994. Protein Engineering 7:1509); rapid amplification of cDNA ends (Ruberti, F. et al. 1994. J. Immunol. Methods 173:33); antibody leader sequences (Larrick et al. 1989 Biochem. Biophys. Res. Commun. 160:1250); or based on known variable region framework amino acid sequences from the Kabat (Kabat et al. 1991. Sequences of Proteins of Immunological Interest. Bethesda, Md.:JS Dep. Health Hum. Serv. $5^{th}$ ed.) or the V-base databases (e.g., Orlandi et al. 1989. Proc. Natl. Acad. Sci. USA 86:3833; Sblattero et al. 1998. Immunotechnology 3:271; or Krebber et al. 1997. J. Immunol. Methods 201:35). Constant region domains can be selected having a particular effector function (or lacking a particular effector function) or with a particular modification to reduce immunogenicity. Variable and constant domains can be cloned, e.g., using the polymerase chain reaction and primers which are selected to amplify the domain of interest. PCR amplification methods are described in detail in U.S. Pat. Nos. 4,683,195; 4,683,202; 4,800,159; 4,965,188; and in, e.g., "PCR Protocols: A Guide to Methods and Applications" Innis et al. eds., Academic Press, San Diego, Calif. (1990); Ho et al. 1989. Gene 77:51; Horton et al. 1993. Methods Enzymol. 217:270).

Alternatively, V domains can be obtained from libraries of V gene sequences from an animal of choice. Libraries expressing random combinations of domains, e.g., VH and VL domains, can be screened with a desired antigen to identify elements which have desired binding characteristics. Methods of such screening are well known in the art. For example, antibody gene repertoires can be cloned into a λ bacteriophage expression vector (Huse, W D et al. 1989. Science 2476:1275). In addition, cells (Boder and Wittrup. 1997. Nat. Biotechnol. 15:553; Daugtherty, P. et al. 2000. J. Immunol. Methods. 243:211; Francisco et al. 1994. Proc. Natl. Acad. Sci. USA 90:10444; Georgiou et al. 1997. Nature Biotechnology 15:29) or viruses (e.g., Hoogenboom, H R 1998 Immunotechnology 4:1 Winter et al. 1994. Annu. Rev. Immunol. 12:433; Griffiths, A D. 1998. Curr. Opin. Biotechnol. 9:102) expressing antibodies on their surface can be screened. Ribosomal display can also be used to screen antibody libraries (Hanes J., et al. 1998. Proc. Natl. Acad. Sci. USA 95:14130; Hanes, J. and Pluckthun. 1999. Curr. Top. Microbiol. Immunol. 243:107; He, M. and Taussig. 1997. Nucleic Acids Research 25:5132).

Preferred libraries for screening are human V gene libraries. VL and VH domains from a non-human source may also be used. In one embodiment, such non-human V domains can be altered to reduce their immunogenicity using art recognized techniques.

Libraries can be naïve, from immunized subjects, or semi-synthetic (Hoogenboom, H. R. and Winter. 1992. J. Mol. Biol. 227:381; Griffiths, A D, et al. EMBO J. 13:3245; de Kruif, J. et al. 1995. J. Mol. Biol. 248:97; Barbas, C. F., et al. 1992. Proc. Natl. Acad. Sci. USA 89:4457).

In addition, the sequences of many antibody V and C domains are known and such domains can be synthesized using methods well known in the art. In one embodiment, mutations can be made to immunoglobulin domains to create a library of nucleic acid molecules having greater heterogeneity (Thompson, J., et al. 1996. J. Mol. Biol. 256:77; Lamminmaki, U. et al. 1999. J. Mol. Biol. 291:589; Caldwell, R. C. and Joyce G F. 1992. PCR Methods Appl. 2:28; Caldwell R C and Joyce G F. 1994. PCR Methods Appl. 3:S136. Standard screening procedures can be used to select high affinity variants. In another embodiment, changes to VH and VL sequences can be made to increase or decrease antibody avidity, e.g., using information obtained from crystal structures using techniques known in the art.

Antigen recognition sites or entire variable regions may be derived from one or more parental antibodies. The parental antibodies can include naturally occurring antibodies or antibody fragments, antibodies or antibody fragments adapted from naturally occurring antibodies, antibodies constructed de novo using sequences of antibodies or antibody fragments known to be specific for GITR. Sequences that may be derived from parental antibodies include heavy and/or light chain variable regions and/or CDRs, framework regions or other portions thereof.

In one embodiment, the GITR binding molecule is a humanized antibody. To make humanized antibodies, animals are immunized with the desired antigen, the corresponding antibodies are isolated, and the portion of the variable region sequences responsible for specific antigen binding is removed. The animal-derived antigen binding regions are then cloned into the appropriate position of human antibody genes in which the antigen binding regions have been deleted. See, e.g. Jones, P. et al. (1986), *Nature* 321, 522-525 or Tempest et al. (1991) *Biotechnology* 9, 266-273. Also, transgenic mice, or other mammals, may be used to express humanized antibodies. Such humanization may be partial or complete. Humanized antibodies minimize the use of heterologous (inter-species) sequences in human antibodies, and are less likely to elicit immune responses in the treated subject.

In one embodiment, a binding molecule of the invention comprises or consists of an antigen binding fragment of an antibody. The term "antigen-binding fragment" refers to a polypeptide fragment of an immunoglobulin or antibody that binds antigen or competes with intact antibody (i.e., with the intact antibody from which they were derived) for antigen binding (i.e., specific binding). As used herein, the term "fragment" of an antibody molecule includes antigen-binding fragments of antibodies, for example, an antibody light chain (VL), an antibody heavy chain (VH), a single chain antibody (scFv), a F(ab')2 fragment, a Fab fragment, an Fd fragment, an Fv fragment, and a single domain antibody fragment (DAb). Fragments can be obtained, e.g., via chemical or enzymatic treatment of an intact or complete antibody or antibody chain or by recombinant means.

In one embodiment, a binding molecule of the invention is an engineered or modified antibody. Engineered forms of antibodies include, for example, minibodies, diabodies, diabodies fused to CH3 molecules, tetravalent antibodies, intradiabodies (e.g., Jendreyko et al. 2003. J. Biol. Chem. 278: 47813), bispecific antibodies, fusion proteins (e.g., antibody cytokine fusion proteins) or, bispecific antibodies. Other immunoglobulins (Ig) and certain variants thereof are described, for example in U.S. Pat. No. 4,745,055; EP 256,654; Faulkner et al., Nature 298:286 (1982); EP 120,694; EP 125,023; Morrison, J. Immun. 123:793 (1979); Kohler et al., Proc. Natl. Acad. Sci. USA 77:2197 (1980); Raso et al., Cancer Res. 41:2073 (1981); Morrison et al., Ann. Rev. Immunol. 2:239 (1984); Morrison, Science 229:1202 (1985); Morrison et al., Proc. Natl. Acad. Sci. USA 81:6851 (1984); EP 255,694; EP 266,663; and WO 88/03559. Reassorted immunoglobulin chains also are known. See, for example, U.S. Pat. No. 4,444,878; WO 88/03565; and EP 68,763 and references cited therein.

In one embodiment, the modified antibodies of the invention are minibodies. Minibodies are dimeric molecules made up of two polypeptide chains each comprising an ScFv molecule (a single polypeptide comprising one or more antigen binding sites, e.g., a VL domain linked by a flexible linker to a VH domain fused to a CH3 domain via a connecting peptide.

ScFv molecules can be constructed in a VH-linker-VL orientation or VL-linker-VH orientation.

The flexible hinge that links the VL and VH domains that make up the antigen binding site preferably comprises from about 10 to about 50 amino acid residues. An exemplary connecting peptide for this purpose is (Gly4Ser)3 (Huston et al. 1988. Proc. Natl. Acad. Sci. USA 85:5879). Other connecting peptides are known in the art.

Methods of making single chain antibodies are well known in the art, e.g., Ho et al. 1989. Gene 77:51; Bird et al. 1988 *Science* 242:423; Pantoliano et al. 1991. *Biochemistry* 30:10117; Milenic et al. 1991. *Cancer Research* 51:6363; Takkinen et al. 1991. *Protein Engineering* 4:837.

Minibodies can be made by constructing an ScFv component and connecting peptide-CH3 component using methods described in the art (see, e.g., U.S. Pat. No. 5,837,821 or WO 94/09817A1). These components can be isolated from separate plasmids as restriction fragments and then ligated and recloned into an appropriate vector. Appropriate assembly can be verified by restriction digestion and DNA sequence analysis.

Diabodies are similar to scFv molecules, but usually have a short (less than 10 and preferably 1-5) amino acid residue linker connecting both V-domains, such that the VL and VH domains on the same polypeptide chain can not interact. Instead, the VL and VH domain of one polypeptide chain interact with the VH and VL domain (respectively) on a second polypeptide chain (WO 02/02781). In one embodiment, a binding molecule of the invention is a diabody fused to at least one heavy chain portion. In a preferred embodiment, a binding molecule of the invention is a diabody fused to a CH3 domain.

Other forms of modified antibodies are also within the scope of the instant invention (e.g., WO 02/02781 A1; 5,959, 083; 6,476,198 B1; US 2002/0103345 A1; WO 00/06605; Byrn et al. 1990. Nature. 344:667-70; Chamow and Ashkenazi. 1996. Trends Biotechnol. 14:52).

In one embodiment, a GITR binding molecule of the invention is modified to alter one or more glycosylation sites or modified by one or more other amino acid substitutions that do not alter one or more glycosylation sites. For example, because the amino acid sequence Asn-X-(Ser/Thr) is a putative consensus sequence for a glycosylation site which may affect the production of the binding molecule, a conservative substitution of a glutamine (Gln) for an asparagine (Asn) may be made.

In one embodiment, a binding molecule of the invention comprises an immunoglobulin constant region. It is known in the art that the constant region mediates several effector functions. For example, binding of the C1 component of complement to binding molecules activates the complement system. Activation of complement is important in the opsonisation and lysis of cell pathogens. The activation of complement also stimulates the inflammatory response and may also be involved in autoimmune hypersensitivity. Further, binding molecules bind to cells via the Fc region, with a Fc receptor site on the binding molecule Fc region binding to a Fc receptor (FcR) on a cell. There are a number of Fc receptors which are specific for different classes of binding molecule, including IgG (gamma receptors), IgE (epsilon receptors), IgA (alpha receptors) and IgM (mu receptors). Binding of binding molecule to Fc receptors on cell surfaces triggers a number of important and diverse biological responses including engulfment and destruction of binding molecule-coated particles, clearance of immune complexes, lysis of binding molecule-coated target cells by killer cells (called antibody-dependent cell-mediated cytotoxicity, or ADCC), release of inflammatory mediators, placental transfer and control of immunoglobulin production.

In one embodiment, effector functions may be eliminated or reduced by, for example, using a constant region of an IgG4 binding molecule, which is thought to be unable to deplete target cells, or making Fc variants, wherein residues in the Fc region critical for effector function(s) are mutated using techniques known in the art, for example, U.S. Pat. No. 5,585,097. For example, the deletion or inactivation (through point mutations or other means) of a constant region domain may reduce Fc receptor binding of the circulating modified binding molecule thereby increasing tumor localization. Additionally, amino acid substitutions to remove potential glycosylation sites on Fc may reduce Fc receptor binding (see, e.g., Shields, et al. (2001) *J Biol Chem* 276:6591). In one embodiment, an N297A substitution is made. In another embodiment, a L235A substitution and a L237A is made. In yet another embodiment, a L234A substitution and a L235A substitution is made. In another embodiment, a E233P substitution is made. In another embodiment, a L234V substitution is made. In another embodiment, a L235A substitution is made. In another embodiment, C236 is deleted. In another embodiment, a P238A substitution is made. In another embodiment, a D265A substitution is made. In another embodiment, a N297A substitution is made. In another embodiment, a A327Q substitution is made. In another embodiment, a P329A substitution is made. The above recited amino acid positions are based on the EU numbering system (see, e.g., Kabat, et al. (1991) *Sequence of Proteins of Immunological Interest*, 5$^{th}$ edition, United States Public Health Service, National Institutes of Health, Bethesda).

In other cases it may be that constant, region modifications consistent with the instant invention moderate complement binding and/or reduce the serum half life. Yet other modifications of the constant region may be used to modify disulfide linkages or oligosaccharide moieties that allow for enhanced localization due to increased antigen specificity or binding molecule flexibility. More generally, those skilled in the art will realize that binding molecules modified as described herein may exert a number of subtle effects that may or may not be readily appreciated. However the resulting physiological profile, bioavailability and other biochemical effects of the modifications, such as tumor localization, biodistribution and serum half-life, may easily be measured and quantified using well know immunological techniques without undue experimentation.

In one embodiment, a binding molecule of the invention can be derivatized or linked to another functional molecule (e.g., another peptide or protein). Accordingly, a binding molecule of the invention include derivatized and otherwise modified forms of the GITR binding molecules described herein, including immunoadhesion molecules. For example, a binding molecule of the invention can be functionally linked (by chemical coupling, genetic fusion, noncovalent association or otherwise) to one or more other molecular entities, such as another binding molecule (e.g., an scFv antibody, a bispecific antibody or a diabody), a detectable agent, a chemotherapeutic agent (e.g., as described herein), a pharmaceutical agent, and/or a protein or peptide that can mediate association of the binding molecule with another molecule (such as a streptavidin core region or a polyhistidine tag).

In one embodiment, a binding molecule of the invention is modified with polyethylene glycol. "PEGylation" increases residence time and reduces immunogenicity in vivo. For example, Knauf et al., J. Biol. Chem., 263: 15064 15070 (1988) reported a study of the pharmacodynamic behavior in rats of various polyoxylated glycerol and polyethylene glycol modified species of interleukin-2. Delgado et al., Br. J. Cancer, 73: 175 182 (1996), Kitamura et al., Cancer Res., 51: 4310 4315 (1991), Kitamura et al., Biochem. Biophys. Res. Comm., 171: 1387 1394 (1990), and Pedley et al., Br. J. Cancer, 70: 1126 1130 (1994) reported studies characterizing blood clearance and tissue uptake of certain anti-tumor antigen antibodies or antibody fragments derivatized with low molecular weight (5 kD) PEG. Zapata et al., FASEB J. 9: A1479 (1995) reported that low molecular weight (5 or 10 kD) PEG attached to a sulfhydryl group in the hinge region of a Fab' fragment reduced clearance compared to the parental Fab' molecule.

One type of derivatized binding molecule is produced by crosslinking two or more binding molecules (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

A binding molecule of the invention can be prepared by recombinant expression of immunoglobulin light and heavy chain genes in a host cell. To express a binding molecule recombinantly, a host cell is transfected with one or more recombinant expression vectors carrying DNA fragments encoding the immunoglobulin light and heavy chains of the binding molecule such that the light and heavy chains are expressed in the host cell and, preferably, secreted into the medium in which the host cells are cultured, from which medium a binding molecule can be recovered. Standard recombinant DNA methodologies are used to obtain antibody heavy and light chain genes, incorporate these genes into recombinant expression vectors, and introduce the vectors into host cells, such as those described in Sambrook, Fritsch and Maniatis (eds), *Molecular Cloning; A Laboratory Manual, Second Edition*, Cold Spring Harbor, N.Y., (1989), Ausubel, F. M. et al. (eds.) *Current Protocols in Molecular Biology*, Greene Publishing Associates, (1989) and in U.S. Pat. No. 4,816,397 by Boss, et al.

To express a binding molecule of the invention, DNAs encoding partial or full-length light and heavy chains may be inserted into expression vector(s) such that the genes are operatively linked to transcriptional and translational control sequences using methods well known in the art. In this context, the term "operatively linked" means that a binding molecule gene is ligated into a vector such that transcriptional and translational control sequences within the vector serve their intended function of regulating the transcription and translation of the binding molecule gene. In one embodiment, the expression vector and expression control sequences are chosen to be compatible with the expression host cell used. The binding molecule light chain gene and the binding molecule heavy chain gene may be inserted into separate vector or, more typically, both genes are inserted into the same expression vector. The binding molecule genes may be inserted into the expression vector by standard methods (e.g., ligation of complementary restriction sites on the binding molecule gene fragment and vector, or blunt end ligation if no restriction sites are present). Prior to insertion of the binding molecule light or heavy chain sequences, the expression vector may already carry binding molecule constant region sequences. For example, one approach to converting VH and VL sequences to full-length binding molecule genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the binding molecule chain from a host cell. The binding molecule chain gene can be cloned into the vector such that the signal peptide is linked in-frame to the amino terminus of the binding molecule chain gene. The signal peptide can be an immunoglobulin signal peptide or a heterologous signal peptide (i.e., a signal peptide from a non-immunoglobulin protein).

In addition to the binding molecule chain genes, the recombinant expression vectors of the invention carry regulatory sequences that control the expression of the binding molecule chain genes in a host cell. The term "regulatory sequence" includes promoters, enhancers and other expression control elements (e.g., polyadenylation signals) that control the transcription or translation of the binding molecule chain genes. Such regulatory sequences are described, for example, in Goeddel; *Gene Expression Technology: Methods in Enzymology* 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP) and polyoma. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner, et al.

In addition to the binding molecule chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification) and the neo gene (for G418 selection).

For expression of the light and heavy chains, the expression vector(s) encoding the binding molecule heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. It is possible to express a binding molecule of the invention in either prokaryotic or eukaryotic host cells, expression of binding molecules in eukaryotic cells, and most preferably mammalian host cells, is the most preferred because such eukaryotic cells, and in particular mammalian cells, are more likely than prokaryotic cells to assemble and secrete a properly folded and immunologically active binding molecule.

Commonly, expression vectors contain selection markers (e.g., ampicillin-resistance, hygromycin-resistance, tetracycline resistance or neomycin resistance) to permit detection of those cells transformed with the desired DNA sequences (see, e.g., Itakura et al., U.S. Pat. No. 4,704,362).

*E. coli* is one prokaryotic host particularly useful for cloning the polynucleotides (e.g., DNA sequences) of the present invention. Other microbial hosts suitable for use include bacilli, such as *Bacillus subtilus*, and other enterobacteriaceae, such as *Salmonella, Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, are also useful for expression. *Saccharomyces* is a preferred yeast host, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian tissue cell culture may also be used to express and produce the polypeptides of the present invention (e.g., polynucleotides encoding binding molecules). See Winnacker, From Genes to Clones, VCH Publishers, N.Y., N.Y. (1987). Eukaryotic cells are actually preferred, because a number of suitable host cell lines capable of secreting heterologous proteins (e.g., intact binding molecules) have been developed in the art, and include CHO cell lines, various Cos cell lines, HeLa cells, myeloma cell lines, or transformed B-cells or hybridomas. Preferably, the cells are nonhuman. Expression vectors for these cells can include expression control sequences, such as an origin of replication, a promoter, and an enhancer (Queen et al., *Immunol. Rev.* 89:49 (1986)), and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, cytomegalovirus and the like. See Co et al., *J. Immunol.* 148:1149 (1992).

Alternatively, binding molecule-coding sequences can be incorporated in transgenes for introduction into the genome of a transgenic animal and subsequent expression in the milk of the transgenic animal (see, e.g., Deboer et al., U.S. Pat. No. 5,741,957, Rosen, U.S. Pat. No. 5,304,489, and Meade et al., U.S. Pat. No. 5,849,992). Suitable transgenes include coding sequences for light and/or heavy chains in operable linkage with a promoter and enhancer from a mammary gland specific gene, such as casein or beta lactoglobulin.

Preferred mammalian host cells for expressing the recombinant binding molecules of the invention include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NS0 myeloma cells, COS cells and SP2 cells. When recombinant expression vectors encoding binding molecule genes are introduced into mammalian host cells, binding molecules are produced by culturing the host cells for a period of time sufficient to allow for expression of the binding molecule in the host cells or, more preferably, secretion of the binding molecule into the culture medium in which the host cells are grown. Binding molecules can be recovered from the culture medium using standard protein purification methods.

The vectors containing the polynucleotide sequences of interest (e.g., the binding molecule heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment, electroporation, lipofection, biolistics or viral-based transfection may be used for other cellular hosts. (See generally Sambrook et al., *Molecular Cloning: A Laboratory Manual* (Cold Spring Harbor Press, 2nd ed., 1989) (incorporated by reference in its entirety for all purposes). Other methods used to transform mammalian cells include the use of polybrene, protoplast fusion, liposomes, electroporation, and microinjection (see generally, Sambrook et al., supra). For production of transgenic animals, transgenes can be microinjected into fertilized oocytes, or can be incorporated into the genome of embryonic stem cells, and the nuclei of such cells transferred into enucleated oocytes.

When heavy and light chains are cloned on separate expression vectors, the vectors are co-transfected to obtain expression and assembly of intact immunoglobulins. Once expressed, the whole binding molecules, their dimers, individual light and heavy chains, or other immunoglobulin forms of the present invention can be purified according to standard procedures of the art, including ammonium sulfate precipitation, affinity columns, column chromatography, HPLC purification, gel electrophoresis and the like (see generally Scopes, Protein Purification (Springer-Verlag, N.Y., (1982)). Substantially pure binding molecules of at least about 90 to 95% homogeneity are preferred, and 98 to 99% or more homogeneity most preferred, for pharmaceutical uses.

Host cells can also be used to produce portions of intact binding molecules, such as Fab fragments or scFv molecules. It will be understood that variations on the above procedure are within the scope of the present invention. For example, it may be desirable to transfect a host cell with DNA encoding either the light chain or the heavy chain (but not both) of a binding molecule of this invention. Recombinant DNA technology may also be used to remove some or all of the DNA encoding either or both of the light and heavy chains that is not necessary for binding to GITR. The molecules expressed from such truncated DNA molecules are also encompassed by a binding molecule of the invention. In addition, bifunctional binding molecules may be produced in which one heavy and one light chain are a binding molecule of the invention and the other heavy and light chain are specific for an antigen other than GITR by crosslinking a binding molecule of the invention to a second binding molecule by standard chemical crosslinking methods.

III. ADDITIONAL AGENTS

In one embodiment, an additional agent for use in the combination therapies of the invention is a chemotherapeutic agent.

Chemotherapeutic agents generally belong to various classes including, for example:

1. Topoisomerase II inhibitors (cytotoxic antibiotics), such as the antracyclines/anthracenediones, e.g., doxorubicin, epirubicin, idarubicin and nemorubicin, the anthraquinones, e.g., mitoxantrone and losoxantrone, and the podophillotoxines, e.g., etoposide and teniposide;

2. Agents that affect microtubule formation (mitotic inhibitors), such as plant alkaloids (e.g., a compound belonging to a family of alkaline, nitrogen-containing molecules derived from plants that are biologically active and cytotoxic), e.g., taxanes, e.g., paclitaxel and docetaxel, and the vinka alkaloids, e.g., vinblastine, vincristine, and vinorelbine, and derivatives of podophyllotoxin;

3. Alkylating agents, such as nitrogen mustards, ethyleneimine compounds, alkyl sulphonates and other compounds with an alkylating action such as nitrosoureas, dacarbazine, cyclophosphamide, ifosfamide and melphalan;

4. Antimetabolites (nucleoside inhibitors), for example, folates, e.g., folic acid, fluoropyrimidines, purine or pyrimidine analogues such as 5-fluorouracil, capecitabine, gemcitabine, methotrexate and edatrexate;

5. Topoisomerase I inhibitors, such as topotecan, irinotecan, and 9-nitrocamptothecin, and camptothecin derivatives; and 6. Platinum compounds/complexes, such as cisplatin, oxaliplatin, and carbopaltin;

Exemplary chemotherapeutic agents for use in the methods of the invention include, but are not limited to, amifostine (ethyol), cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), doxorubicin lipo (doxil), gemcitabine (gemzar), daunorubicin, daunorubicin lipo (daunoxome), procarbazine, mitomycin, cytarabine, etoposide, methotrexate, 5-fluorouracil (5-FU), vinblastine, vincristine, bleomycin, paclitaxel (taxol), docetaxel (taxotere), aldesleukin, asparaginase, busulfan, carboplatin, cladribine, camptothecin, CPT-11, 10-hydroxy-7-ethyl-camptothecin (SN38), dacarbazine, S-I capecitabine, ftorafur, 5'deoxyfluorouridine, UFT, eniluracil, deoxycytidine, 5-azacytosine, 5-azadeoxycytosine, allopurinol, 2-chloro adenosine, trimetrexate, aminopterin, methylene-10-deazaminopterin (MDAM), oxaplatin, picoplatin, tetraplatin, satraplatin, platinum-DACH, ormaplatin, CI-973, JM-216, and analogs thereof, epirubicin, etoposide phosphate, 9-aminocamptothecin, 10,11-methylenedioxycamptothecin, karenitecin, 9-nitrocamptothecin, TAS 103, vindesine, L-phenylalanine mustard, ifosphamidemefosphamide, perfosfamide, trophosphamide carmustine, semustine, epothilones A-E, tomudex, 6-mercaptopurine, 6-thioguanine, amsacrine, etoposide phosphate, karenitecin, acyclovir, valacyclovir, ganciclovir, amantadine, rimantadine, lamivudine, zidovudine, bevacizumab, trastuzumab, rituximab, 5-Fluorouracil, Capecitabine, Pentostatin, Trimetrexate, Cladribine, floxuridine, fludarabine, hydroxyurea, ifosfamide, idarubicin, mesna, irinotecan, mitoxantrone, topotecan, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil, cisplatin, doxorubicin, paclitaxel (taxol) and bleomycin, and combinations thereof which are readily apparent to one of skill in the art based on the appropriate standard of care for a particular tumor or cancer.

In one embodiment, a chemotherapeutic agent for use in the combination therapies of the invention is selected from the group consisting of Gemzar, 5-FU, Vincristine, Vinblastine, Adriamycin, Cisplatin, Taxol, Thalidomide, Velcade, methotrexate, cytarabine, fludarabine, hyroxyurea, danorubracin, etopside, mitoxantrone, chlorambucil, cyclophosphamide, melphelan, thiotepa, bleomycin, dacarbazine, L-asparaginase, and procarbazine.

In one embodiment, a chemotherapeutic agent is a topoisomerase II inhibitor. In another embodiment, a chemotherapeutic agent is an agent that affects microtubule formation. In another embodiment, a chemotherapeutic agent is an alkylating agent. In another embodiment, a chemotherapeutic agent is a topoisomerase I inhibitor. In another embodiment, a chemotherapeutic agent is a platinum compound/complex. In another embodiment, a chemotherapeutic agent is a hormone, hormonal analogue, and/or hormonal complex. In another embodiment, a chemotherapeutic agent is an enzyme, protein, peptide, polyclonal and/or monoclonal antibody. In one embodiment, the chemotherapeutic agent for use in the methods of the invention is an antimetabolite.

The term "antimetabolite" refers to a substance which is structurally similar to a critical natural intermediate (metabolite) in a biochemical pathway leading to DNA or RNA synthesis which is used by the host in that pathway, but acts to inhibit the completion of that pathway (i.e., synthesis of DNA or RNA). More specifically, antimetabolites typically function by (1) competing with metabolites for the catalytic or regulatory site of a key enzyme in DNA or RNA synthesis, or (2) substitute for a metabolite that is normally incorporated into DNA or RNA, and thereby producing a DNA or RNA that cannot support replication. Major categories of antimetabolites include (1) folic acid analogs, which are inhibitors of dihydrofolate reductase (DHFR); (2) purine analogs, which mimic the natural purines (adenine or guanine) but are structurally different so they competitively or irreversibly inhibit nuclear processing of DNA or RNA; and (3) pyrimidine analogs, which mimic the natural pyrimidines (cytosine, thymidine, and uracil), but are structurally different so thy competitively or irreversibly inhibit nuclear processing of DNA or RNA. Non-limiting examples of antimetabolites of this invention are 5-Fluorouracil, Floxuradine, Thioguanine, Cytarabine, Fludarabine, 6-Mercaptopurine, Methotrexate, Gemcitabine, Capecitabine, Pentostatin, Trimetrexate, and Cladribine.

In one embodiment, the antimetabolite is the nucleoside analog gemcitabine. In another embodiment, the antimetabolite is the nucleoside analog fluorouracil.

As used herein, an "agent that affects microtubule formation" or "mitotic inhibitor" is an agent that disrupts microtubule polymerization. Mitotic inhibitors work by interfering with and halting mitosis (usually during the M phase of the cell cycle), so that the cell will no longer divide. In one embodiment, an agent that affects microtubule formation is paclitaxol (Taxol®).

As used herein, an "alkylating agent" is an agent that cross-links guanine nucleobases in DNA making the strands unable to uncoil and separate. As this is necessary in DNA replication, the cells can no longer divide. In one embodiment, an alkylating agent is cyclophosphamide, also known as cytophosphane. Cyclophosphamide is a prodrug.

In another embodiment, an additional agent for use in the combination therapies of the invention is a biologic agent.

Biological agents (also called biologics) are the products of a biological system, e.g., an organism, cell, or recombinant system. Examples of such biologic agents include nucleic acid molecules (e.g., antisense nucleic acid molecules), interferons, interleukins, colony-stimulating factors, antibodies, e.g., monoclonal antibodies, anti-angiogenesis agents, and cytokines. Exemplary biologic agents are discussed in more detail below and generally belong to various classes including, for example 1. Hormones, hormonal analogues, and hormonal complexes, e.g., estrogens and estrogen analogs, progesterone, progesterone analogs and progestins, androgens, adrenocorticosteroids, antiestrogens, antiandrogens, antitestosterones, adrenal steroid inhibitors, and anti-leuteinizing hormones; and 2. Enzymes, proteins, peptides, polyclonal and/or monoclonal antibodies, such as interleukins, interferons, colony stimulating factor, etc.

In one embodiment, the biologic is an interfereon. Interferons (IFN) are a type biologic agent that naturally occurs in the body. Interferons are also produced in the laboratory and given to cancer patients in biological therapy. They have been shown to improve the way a cancer patient's immune system acts against cancer cells. Interferons may work directly on cancer cells to slow their growth, or they may cause cancer cells to change into cells with more normal behavior. Some interferons may also stimulate natural killer cells (NK) cells, T cells, and macrophages—types of white blood cells in the bloodstream that help to fight cancer cells.

In one embodiment, the biologic is an interleukin. Interleukins (IL) stimulate the growth and activity of many immune cells. They are proteins (cytokines and chemokines) that occur naturally in the body, but can also be made in the laboratory. Some interleukins stimulate the growth and activity of immune cells, such as lymphocytes, which work to destroy cancer cells.

In another embodiment, the biologic is a colony-stimulating factor. Colony-stimulating factors (CSFs) are proteins given to patients to encourage stem cells within the bone marrow to produce more blood cells. The body constantly needs new white blood cells, red blood cells, and platelets, especially when cancer is present. CSFs are given, along with chemotherapy, to help boost the immune system. When cancer patients receive chemotherapy, the bone marrow's ability to produce new blood cells is suppressed, making patients more prone to developing infections. Parts of the immune system cannot function without blood cells, thus colony-stimulating factors encourage the bone marrow stem cells to produce white blood cells, platelets, and red blood cells. With proper cell production, other cancer treatments can continue enabling patients to safely receive higher doses of chemotherapy.

In another embodiment, the biologic is an antibody. Antibodies, e.g., monoclonal antibodies, are agents, produced in the laboratory, that bind to cancer cells. When cancer-destroying agents are introduced into the body, they seek out the antibodies and kill the cancer cells. Monoclonal antibody agents do not destroy healthy cells. Monoclonal antibodies achieve their therapeutic effect through various mechanisms. They can have direct effects in producing apoptosis or programmed cell death. They can block growth factor receptors, effectively arresting proliferation of tumor cells. In cells that express monoclonal antibodies, they can bring about anti-idiotype antibody formation.

Examples of antibodies which may be used in the combination treatment of the invention include anti-CD20 antibodies, such as, but not limited to, cetuximab, Tositumomab, rituximab, and Ibritumomab. Anti-HER2 antibodies may also be used in combination with an anti-GITR antibody for the treatment of cancer. In one embodiment, the anti-HER2 antibody is Trastuzumab (Herceptin). Other examples of antibodies which may be used in combination with an anti-GITR antibody for the treatment of cancer include anti-CD52 antibodies (e.g., Alelmtuzumab), anti-CD-22 antibodies (e.g., Epratuzumab), and anti-CD33 antibodies (e.g., Gemtuzumab ozogamicin). Anti-VEGF antibodies may also be used in combination with an anti-GITR antibody for the treatment of cancer. In one embodiment, the anti-VEGF antibody is bevacizumab. In other embodiments, the biologic agent is an antibody which is an anti-EGFR antibody e.g., cetuximab. Another example is the anti-glycoprotein 17-1A antibody edrecolomab.

In another embodiment, the biologic is a cytokine. Cytokine therapy uses proteins (cytokines) to help a subject's immune system recognize and destroy those cells that are cancerous. Cytokines are produced naturally in the body by the immune system, but can also be produced in the laboratory. This therapy is used with advanced melanoma and with adjuvant therapy (therapy given after or in addition to the primary cancer treatment). Cytokine therapy reaches all parts of the body to kill cancer cells and prevent tumors from growing.

In another embodiment, the biologic is a fusion protein. Fusion proteins may also be used. For example, recombinant human Apo2L/TRAIL (Genentech) may be used in a combination therapy. Apo2/TRAIL is the first dual pro-apoptotic receptor agonist designed to activate both pro-apoptotic receptors DR4 and DR5, which are involved in the regulation of apoptosis (programmed cell death).

In one embodiment, the biologic is an antisense nucleic acid molecule. Antisense nucleic acid molecules may also be used in the methods of the invention. As used herein, an "antisense" nucleic acid comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid can hydrogen bond to a sense nucleic acid.

In one embodiment, a biologic agent is an siRNA molecule, e.g., of a molecule that enhances angiogenesis, e.g., bFGF, VEGF and EGFR. In one embodiment, a biologic agent that inhibits angiogenesis mediates RNAi. RNA interference (RNAi) is a post-transcriptional, targeted gene-silencing technique that uses double-stranded RNA (dsRNA) to degrade messenger RNA (mRNA) containing the same sequence as the dsRNA (Sharp, P. A. and Zamore, P. D. 287, 2431-2432 (2000); Zamore, P. D., et al. Cell 101, 25-33 (2000). Tuschl, T. et al. Genes Dev. 13, 3191-3197 (1999); Cottrell T R, and Doering T L. 2003. Trends Microbiol. 11:37-43; Bushman F. 2003. Mol. Therapy. 7:9-10; McManus M T and Sharp P A. 2002. Nat Rev Genet. 3:737-47). The process occurs when an endogenous ribonuclease cleaves the longer dsRNA into shorter, e.g., 21- or 22-nucleotide-long RNAs, termed small interfering RNAs or siRNAs. The smaller RNA segments then mediate the degradation of the target mRNA. Kits for synthesis of RNAi are commercially available from, e.g. New England Biolabs or Ambion. In one embodiment one or more of the chemistries described herein for use in antisense RNA can be employed in molecules that mediate RNAi.

The use of antisense nucleic acids to downregulate the expression of a particular protein in a cell is well known in the art (see e.g., Weintraub, H. et al., Antisense RNA as a molecular tool for genetic analysis, Reviews—Trends in Genetics, Vol. 1(1) 1986; Askari, F. K. and McDonnell, W. M. (1996) N. Eng. J. Med. 334:316-318; Bennett, M. R. and Schwartz, S. M. (1995) Circulation 92:1981-1993; Mercola, D. and Cohen, J. S. (1995) Cancer Gene Ther. 2:47-59; Rossi, J. J. (1995) Br. Med. Bull. 51:217-225; Wagner, R. W. (1994) Nature 372:333-335). An antisense nucleic acid molecule comprises a nucleotide sequence that is complementary to the coding strand of another nucleic acid molecule (e.g., an mRNA sequence) and accordingly is capable of hydrogen bonding to the coding strand of the other nucleic acid molecule. Antisense sequences complementary to a sequence of an mRNA can be complementary to a sequence found in the coding region of the mRNA, the 5' or 3' untranslated region of the mRNA or a region bridging the coding region and an untranslated region (e.g., at the junction of the 5' untranslated region and the coding region). Furthermore, an antisense nucleic acid can be complementary in sequence to a regulatory region of the gene encoding the mRNA, for instance a transcription initiation sequence or regulatory element. Preferably, an antisense nucleic acid is designed so as to be complementary to a region preceding or spanning the initiation codon on the coding strand or in the 3' untranslated region of an mRNA.

Given the coding strand sequences of a molecule that enhances angiogenesis, antisense nucleic acids of the invention can be designed according to the rules of Watson and Crick base pairing. The antisense nucleic acid molecule can be complementary to the entire coding region of the mRNA, but more preferably is an oligonucleotide which is antisense to only a portion of the coding or noncoding region of the mRNA. For example, the antisense oligonucleotide can be complementary to the region surrounding the translation start site of the mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3=amino-3-N-2-carboxypropyl) uracil, (acp3)w, and 2,6-diaminopurine. To inhibit expression in cells, one or more antisense oligonucleotides can be used. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) Nucleic Acids. Res. 15:6625-6641). The antisense nucleic acid molecule can also comprise a 2'-o-methylribonucleotide (Inoue et al. (1987) Nucleic Acids Res. 15:6131-6148) or a chimeric RNA-DNA analogue (Inoue et al. (1987) FEBS Lett. 215:327-330).

In another embodiment, an antisense nucleic acid of the invention is a compound that mediates RNAi. RNA interfering agents include, but are not limited to, nucleic acid molecules including RNA molecules which are homologous to the target gene or genomic sequence, "short interfering RNA" (siRNA), "short hairpin" or "small hairpin RNA" (shRNA), and small molecules which interfere with or inhibit expression of a target gene by RNA interference (RNAi). RNA interference is a post-transcriptional, targeted gene-silencing technique that uses double-stranded RNA (dsRNA) to degrade messenger RNA (mRNA) containing the same sequence as the dsRNA (Sharp, P. A. and Zamore, P. D. 287, 2431-2432 (2000); Zamore, P. D., et al. Cell 101, 25-33 (2000). Tuschl, T. et al. Genes Dev. 13, 3191-3197 (1999)). The process occurs when an endogenous ribonuclease cleaves the longer dsRNA into shorter, 21- or 22-nucleotide-long RNAs, termed small interfering RNAs or siRNAs. The smaller RNA segments then mediate the degradation of the target mRNA. Kits for synthesis of RNAi are commercially available from, e.g. New England Biolabs and Ambion. In one embodiment one or more of the chemistries described above for use in antisense RNA can be employed.

Nucleic acid molecules encoding molecules that, e.g., inhibit angiogenesis, may be introduced into the subject in a form suitable for expression of the encoded protein in the cells of the subject may also be used in the methods of the invention. Exemplary molecules that inhibit angiogenesis include, but are not limited to, TSP-1, TSP-2, IFN-α, IFN-γ, angiostatin, endostsin, tumastatin, canstatin, VEGI, PEDF, vasohibin, and the 16 kDa fragment of prolactin 2-Methoxyestradiol (see, Kerbel (2004) J. Clin Invest 114:884, for review).

For example, a full length or partial cDNA sequence is cloned into a recombinant expression vector and the vector is transfected into a cell using standard molecular biology techniques. The cDNA can be obtained, for example, by amplification using the polymerase chain reaction (PCR) or by screening an appropriate cDNA library. The nucleotide sequences of the cDNA can be used for the design of PCR primers that allow for amplification of a cDNA by standard PCR methods or for the design of a hybridization probe that can be used to screen a cDNA library using standard hybridization methods. Following isolation or amplification of the cDNA, the DNA fragment is introduced into a suitable expression vector.

Exemplary biologic agents for use in the methods of the invention include, but are not limited to, gefitinib (Iressa), anastrazole, diethylstilbesterol, estradiol, premarin, raloxifene, progesterone, norethynodrel, esthisterone, dimesthisterone, megestrol acetate, medroxyprogesterone acetate, hydroxyprogesterone caproate, norethisterone, methyltestosterone, testosterone, dexamthasone, prednisone, Cortisol, solumedrol, tamoxifen, fulvestrant, toremifene, aminoglutethimide, testolactone, droloxifene, anastrozole, bicalutamide, flutamide, nilutamide, goserelin, flutamide, leuprolide, triptorelin, aminoglutethimide, mitotane, goserelin, cetuximab, erlotinib, imatinib, Tositumomab, Alemtuzumab, Trastuzumab, Gemtuzumab, Rituximab, Ibritumomab tiuxetan, Bevacizumab, Denileukin diftitox, Daclizumab, interferon alpha, interferon beta, anti-4-1BB, anti-4-1BBL, anti-CD40, anti-CD154, anti-OX40, anti-OX40L, anti-CD28, anti-CD80, anti-CD86, anti-CD70, anti-CD27, anti-HVEM, anti-LIGHT, anti-GITRL, anti-CTLA-4, soluble OX40L, soluble 4-1BBL, soluble CD154, soluble GITRL, soluble LIGHT, soluble CD70, soluble CD80, soluble CD86, soluble CTLA4-Ig, GVAX®, and combinations thereof which are readily apparent to one of skill in the art based on the appropriate standard of care for a particular tumor or cancer. The soluble forms of agents may be made as, for example fusion proteins, by operatively linking the agent with, for example, Ig-Fc region.

It should be noted that more than one additional agent, e.g., 1, 2, 3, 4, 5, may be administered in combination with a GITR binding molecule. For example, in one embodiment two chemotherapeutic agents may be administered in combination with a GITR binding molecule. In another embodiment, a chemotherapeutic agent, a biologic agent, and a GITR binding molecule may be administered.

Various forms of the biologic agents may be used. These include, without limitation, such forms as proform molecules, uncharged molecules, molecular complexes, salts, ethers, esters, amides, and the like, which are biologically activated when implanted, injected or otherwise inserted into the tumor.

IV. THERAPEUTIC METHODS

The present invention further provides methods of administering to the subject a combination therapy of the invention.

As set forth above, the methods of the present invention, i.e., the use of a GITR binding molecule in combination with a second agent that is useful in treating cancer, may be used to treat a malignancy or cancer in a subject. Exemplary cancers include: pancreatic cancer, melanoma, breast cancer, lung cancer, bronchial cancer, colorectal cancer, prostate cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, and cancer of hematological tissues.

In one embodiment, the methods of the invention may be used to treat melanoma. In another embodiment, the methods of the invention may be used to treat solid tumors, e.g., a carcinoma. Examples of solid tumors that can be treated by compounds of the present invention, include but are not limited to breast, testicular, lung, ovary, uterine, cervical, pancreatic, non small cell lung (NSCLC), colon, as well as prostate, gastric, skin, stomach, esophagus and bladder cancer. In one embodiment, a solid tumor is an adenocarcinoma, e.g., of the colon. In one embodiment of the invention, a solid tumor is a colon tumor. In another embodiment of the invention, a solid tumor is selected from the group consisting of a colon tumor, a lung tumor, a breast tumor, a stomach tumor, a prostate tumor, a cervical tumor, a vaginal tumor, and a pancreatic tumor.

In another embodiment, the tumor is selected from the group consisting of Stage I, Stage II, Stage III, and Stage IV tumors. The stage of a tumor is readily determined by one of skill in the art using art recognized methods of staging, such as the size of the tumor, the number of lymph nodes or other tissues to which the tumor has metastasized, microscopic analyses, histological analyses, etc.

In one embodiment of the invention, the subject combination therapies are used to treat established tumors, e.g., tumors of sufficient size such that nutrients can no longer permeate to the center of the tumor from the subject's vasculature by osmosis and therefore the tumor requires its own vascular supply to receive nutrients, i.e, a vascularized tumor. In another embodiment, the subject combination therapies are used to treat, e.g., inhibit the establishment of secondary tumor, e.g., metastasis, and/or reduce the size of a tumor, e.g., an established tumor, and/or a secondary tumor, e.g., a metastasis. In yet another embodiment, the subject combination therapies are used to prevent the establishment of secondary tumors, e.g., metastasis.

In one embodiment, a combination therapy is used to treat a tumor having dimensions of at least about 1 mm×1 mm. In another embodiment of the invention, a combination therapy is used to treat a tumor that is at least about 0.5 mm×0.5 mm. In other embodiments of the invention the tumor has a volume of at least about 100 mm$^3$. In one embodiment, a combination therapy of the invention is used to treat a tumor that is large enough to be found by palpation or by imaging techniques well known in the art, such as MRI, ultrasound, or CAT scan.

In certain embodiments of the invention, the subject methods result in an inhibition of tumor size more than about 10%, more than about 20%, more than about 30%, more than about 35%, more than about 42%, more than about 43%, more than about 44%, more than about 45%, more than about 46%, more than about 47%, more than about 48%, more than about 49%, more than about 50%, more than about 51%, more than about 52%, more than about 53%, more than about 54%, more than about 55%, more than about 56%, more than about 57%, more than about 58%, more than about 59%, more than about 60%, more than about 65%, more than about 70%, more than about 75%, more than about 80%, more than about 85%, more than about 90%, more than about 95%, or more than about 100%. In one embodiment, the administration of a GITR binding molecule, or an antigen-binding fragment thereof, and at least one chemotherapeutic agent results in a % T/C of about 42% or greater.

In one embodiment, the combination therapies of the invention have a synergistic effect. A "synergistic effect" of two compounds is one in which the effect of the combination of the two agents is greater than the sum of their individual effects and is statistically different from the controls and the single drugs. In another embodiment, the combination therapies of the invention have an additive effect. An "additive effect" of two compounds is one in which the effect of the combination of the two agents is the sum of their individual effects and is statistically different from either the controls and/or the single drugs.

The GITR binding molecule can be administered in a convenient manner such as by injection (subcutaneous, intravenous, etc.), oral administration, inhalation, transdermal application, or rectal administration. Depending on the route of administration, the active compound can be coated in a material to protect the compound from the action of enzymes, acids and other natural conditions which may inactivate the compound. For example, to administer the agent by other than parenteral administration, it may be desirable to coat, or co-administer the agent with, a material to prevent its inactivation.

In general, the at least one additional agent to be administered in combination with the GITR binding molecule will be administered via the route by which it is routinely administered when used alone. It will be understood that the GITR binding molecule and the at least one additional agent need not be administered via the same route.

A combination therapy of the present invention can be administered by a variety of methods known in the art, although for many therapeutic applications, the preferred route/mode of administration is intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

In certain embodiments, a binding molecule of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

In certain embodiments, the method comprises parenterally administering an effective amount of a GITR binding molecule and a second agent to a subject. In one embodiment, the method comprises intraarterial administration of a GITR binding molecule and at least one chemotherapeutic agent to a subject. In other embodiments, the method comprises administering an effective amount of a GITR binding molecule and at least one chemotherapeutic agent directly to the arterial blood supply of a tumor in a subject. In one embodiment, the methods comprise administering an effective amount of a GITR binding molecule and at least one chemotherapeutic agent directly to the arterial blood supply of the cancerous tumor using a catheter. In embodiments where a catheter is used to administer a GITR binding molecule and at least one chemotherapeutic agent, the insertion of the catheter may be guided or observed by fluoroscopy or other method known in the art by which catheter insertion may be observed and/or guided. In another embodiment, the method comprises chemoembolization. For example a chemoembolization method may comprise blocking a vessel feeding the cancerous tumor with a composition comprised of a resin-like material mixed with an oil base (e.g., polyvinyl alcohol in Ethiodol) and one or more chemotherapeutic agents. In still other embodiments, the method comprises systemic administration of a GITR binding molecule and at least one chemotherapeutic agent to a subject.

In general, chemoembolization or direct intraarterial or intravenous injection therapy utilizing pharmaceutical compositions of the present invention is typically performed in a similar manner, regardless of the site. Briefly, angiography (a road map of the blood vessels), or more specifically in certain embodiments, arteriography, of the area to be embolized may be first performed by injecting radiopaque contrast through a catheter inserted into an artery or vein (depending on the site to be embolized or injected) as an X-ray is taken. The catheter may be inserted either percutaneously or by surgery. The blood vessel may be then embolized by refluxing pharmaceutical compositions of the present invention through the catheter, until flow is observed to cease. Occlusion may be confirmed by repeating the angiogram. In embodiments where direct injection is used, the blood vessel is then infused with a pharmaceutical composition of the invention in the desired dose.

Embolization therapy generally results in the distribution of compositions containing inhibitors throughout the interstices of the tumor or vascular mass to be treated. The physical bulk of the embolic particles clogging the arterial lumen results in the occlusion of the blood supply. In addition to this effect, the presence of an anti-angiogenic factor(s) prevents the formation of new blood vessels to supply the tumor or vascular mass, enhancing the devitalizing effect of cutting off the blood supply. Direct intraarterial, intravenous or injection administration generally results in distribution of compositions containing inhibitors throughout the interstices of the tumor or vascular mass to be treated as well. However, the blood supply is not generally expected to become occluded with this method.

In one aspect of the present invention, primary and secondary tumors may be treated utilizing embolization or direct intraarterial or intravenous injection therapy. Briefly, a catheter is inserted via the femoral or brachial artery and advanced into the, e.g., hepatic artery, by steering it through the arterial system under fluoroscopic guidance. The catheter is advanced into the hepatic arterial tree as far as necessary to allow complete blockage of the blood vessels supplying the tumor(s), while sparing as many of the arterial branches supplying normal structures as possible. Ideally this will be a segmental branch of the hepatic artery, but it could be that the entire hepatic artery distal to the origin of the gastroduodenal artery, or even multiple separate arteries, will need to be blocked depending on the extent of tumor and its individual blood supply. Once the desired catheter position is achieved, the artery is embolized by injecting compositions (as described above) through the arterial catheter until flow in the artery to be blocked ceases, preferably even after observation for 5 minutes. Occlusion of the artery may be confirmed by injecting radio-opaque contrast through the catheter and demonstrating by fluoroscopy or X-ray film that the vessel which previously filled with contrast no longer does so. In embodiments where direct injection is used, the artery is infused by injecting compositions (as described above) through the arterial catheter in a desired dose. The same procedure may be repeated with each feeding artery to be occluded.

With respect to dosing, it is to be noted that dosage amounts, number of cycles administered, and the sequence of administration may vary with the severity of the condition to be alleviated. It is to be further understood that for any particular subject, specific dosage regimens may be adjusted over time according to the individual need and the professional judgment of the person administering or supervising the administration of the compositions. Typically, dosing will be determined using techniques known to one skilled in the art. The selected dosage level will depend upon a variety of factors including the activity of the agent, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health, disease state, the ability of the binding molecule to elicit a desired response in the individual, and prior medical history of the patient being treated, and like factors well known in the medical arts.

Dosage regimens may be adjusted to provide the optimum desired response. For example, a single bolus may be administered, several divided doses may be administered over time or the dose may be proportionally reduced or increased as indicated by the exigencies of the therapeutic situation. In one embodiment, one or more of the agents to be administered may be formulated as a parenteral composition in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

A physician or veterinarian having ordinary skill in the art can readily determine and prescribe the effective amount of each of the agents of the subject combination therapy. For example, the physician or veterinarian could administer at least one additional agent at the dose at which it would be administered to the subject if it were to be administered alone, or as part of a combination therapy that does not employ a GITR binding molecule. Such art recognized dosing protocols can be determined by the skilled artisan without undue experimentation.

The combined use of a GITR binding molecule and at least one chemotherapeutic agent as described herein, may reduce the required dosage for any individual agent. Accordingly, in one embodiment, the dose of at least one additional agent may be lower than that required in order to achieve the desired therapeutic effect were the agent to be administered alone.

With respect to GITR binding molecules, one of ordinary skill in the art would also readily be able to determine an optimal dose. For example, an anti-GITR antibody could be administered at a dose of between about 50 mg/kg and about 0.05 mg/kg. In one embodiment, an anti-GITR antibody could be administered at a dose of between about 40 mg/kg and about 0.1 mg/kg. In another embodiment, an anti-GITR antibody could be administered at a dose of between about 30 mg/kg and about 0.5 mg/kg. In still another embodiment, an anti-GITR antibody could be administered at a dose of between about 20 mg/kg and about 1 mg/kg. Ranges intermediate to the above recited values are also intended to be part of this invention. In yet another embodiment, an anti-GITR antibody could be administered at a dose of between about 10 mg/kg and about 5 mg/kg. For example, exemplary doses include: about 0.06, about 0.07, about 0.08, about 0.09, about 0.1, about 0.2, about 0.3, about 0.4, about 0.5, about 0.6, about 0.7, about 0.8, about 0.9, about 1, about 1.5, about 2, about 2.5, about 3, about 3.5, about 4, about 4.5, about 5, about 10, about 20, about 30, or about 40 mg/kg. It is noted that the dosages and dosage ranges set forth herein are exemplary only and are not intended to limit the scope or practice of the claimed composition.

Data obtained from cell culture assays and animal studies may be used in formulating a range of dosage for use in humans by for example, determining the dose at which no adverse effects occur in, for example, a mouse, and determining the human equivalent dosage (see, e.g., www.fda.gov/cber/gdlns/dose.htm, the contents of which are incorporated herein by reference). The dosage of any supplement, or alternatively of any components therein, lies preferably within a range of circulating concentrations that include the ED50 (median effective dose) with little or no toxicity. The dosage may vary within this range depending upon the dosage form employed and the route of administration utilized. For agents of the present invention, the therapeutically effective dose may be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information may be used to more accurately determine useful doses in humans. Levels in plasma may be measured, for example, by high performance liquid chromatography.

Alternatively, the dosage of the subject invention may be determined by reference to the plasma concentrations of the composition. For example, the maximum plasma concentration (Cmax) and the area under the plasma concentration-time curve from time 0 to infinity (AUC (0-4)) may be used. Dosages for the present invention include those that produce the above values for Cmax and AUC (0-4) and other dosages resulting in larger or smaller values for those parameters.

The precise time of administration and amount of any particular compound that will yield the most effective treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

In one embodiment, the at least one non-GITR binding agent of the combination therapy is administered to a subject prior to administration of the GITR binding molecule. The non-GITR binding molecule may be administered once or more than once to the patient. In cases of repeat administration, the non-GITR binding molecule may be administered daily, on alternative days, weekly, monthly, or according to another schedule. An exemplary treatment entails administration in multiple dosages over a prolonged period, for example, of at least six months.

Similarly, a GITR binding molecule of the invention may be administered once or more than once to a subject. In cases of repeat administration, the GITR binding molecule may be administered daily, on alternative days, weekly, monthly, or according to another schedule. An exemplary treatment entails administration in multiple dosages over a prolonged period, for example, of at least six months.

In instances when the non-GITR binding molecule is administered prior to or after the administration of the GITR binding molecule, intervals between administration of the agents can be, e.g., minutes, hours, days, weeks, or months.

A combination therapy of the invention comprising a GITR binding molecule and at least one additional agent may optionally include administration of additional agents or treatment regimes, e.g., surgery, radiation therapy, that are effective in treating cancer. Preferred additional agents are those which are art recognized and are routinely administered to treat a particular disorder.

While the subject is being treated, the health of the patient may be monitored by measuring one or more of the relevant indices at predetermined times, e.g., during a 24-hour period. Treatment, including supplement, amounts, times of administration and formulation, may be optimized according to the results of such monitoring. The patient may be periodically reevaluated to determine the extent of improvement by measuring the same parameters, the first such reevaluation typically occurring at the end of four weeks from the onset of therapy, and subsequent reevaluations occurring every four to eight weeks during therapy and then every three months thereafter. Therapy may continue for several months or even years, with a minimum of one month being a typical length of therapy for humans. Adjustments to the amount(s) of agent administered and possibly to the time of administration may be made based on these reevaluations.

In one embodiment, the GITR binding molecule and the second agent are conjugated using methods known in the art.

V. KITS OF THE INVENTION

The present invention provides kits and articles of manufacture for use of the methods of the present invention. The invention also pertains to packaged pharmaceutical compositions or kits for administering the GITR binding molecule and a second agent used in the invention for the treatment of cancer. In one embodiment of the invention, the kit or article of manufacture, comprises a GITR binding molecule, and instructions for administration for treatment of cancer in combination with at least one additional agent, e.g., a chemotherapeutic agent. In another embodiment, the kit comprises a second container comprising at least one additional agent for use in a combination therapy with the GITR binding molecule. The instructions may describe how, e.g., intravenously, and when, e.g., at week 0 and week 2, the different doses of GITR binding molecule and at least one chemotherapeutic agent shall be administered to a subject for treatment.

The package or kit alternatively can contain the GITR binding molecule and it can be promoted for use, either within the package or through accompanying information, for the uses or treatment of the disorders described herein. The packaged pharmaceuticals or kits further can include a chemotherapeutic agent (as described herein) packaged with or co-promoted with instructions for using the second agent, e.g., a chemotherapeutic agent, with a first agent, e.g. a GITR binding molecule.

For example, a kit may comprise a packaging material, one or more GITR binding molecules and at least one chemotherapeutic agent as described above and optionally a label or package insert. In still other embodiments, the invention provides a kit comprising one or more GITR binding molecules and at least one chemotherapeutic agent and one or more devices for accomplishing administration of such compositions. For example, a kit may comprise a pharmaceutical composition comprising a GITR binding molecule and catheter for accomplishing direct intraarterial injection of the composition into a solid tumor. The kits optionally include accessory components such as a second container comprising a pharmaceutically-acceptable buffer and instructions for using the composition.

This invention is further illustrated by the following examples, which should not be construed as limiting. The contents of all references, patents and published patent applications cited throughout this application, as well as the Figures, are incorporated herein by reference.

EXAMPLES

Example 1

The Combination of a GITR Binding Molecule and a Nucleoside Analog Decreases Tumor Burden and Increases Survival Time in an Animal Model of Colon Carcinoma Mice were injected in the flank with $1 \times 10^5$ CT26 cells and divided into groups. One group of control mice was untreated. The group of mice receiving Gemzar was treated with 80 mg/kg Gemzar on Day 15. One group of mice received anti-GITR antibody (2F8) alone at a dose of 0.4 mg (I.P.) on Days 15, 16 and 17. The group of mice receiving Gemzar+2F8 were given 80 mg/kg Gemzar on Day 15 and 0.4 mg of 2F8 (I.P.) on Day 16.

The size of the tumors and the survival of the mice were monitored. GraphPad Prism 4 software was used to plot Kaplan-Meir survival curves and to confirm the median survival times for the groups. Tumors were measured using calipers, and tumor size was calculated using the formula $(L \times W^2)/2$.

Tumor burden in mice treated with the combination of Gemzar and 2F8 was reduced as compared to the tumor burden of mice treated with vehicle, Gemzar alone, or 2F8 alone (FIG. 1).

Figure 2:
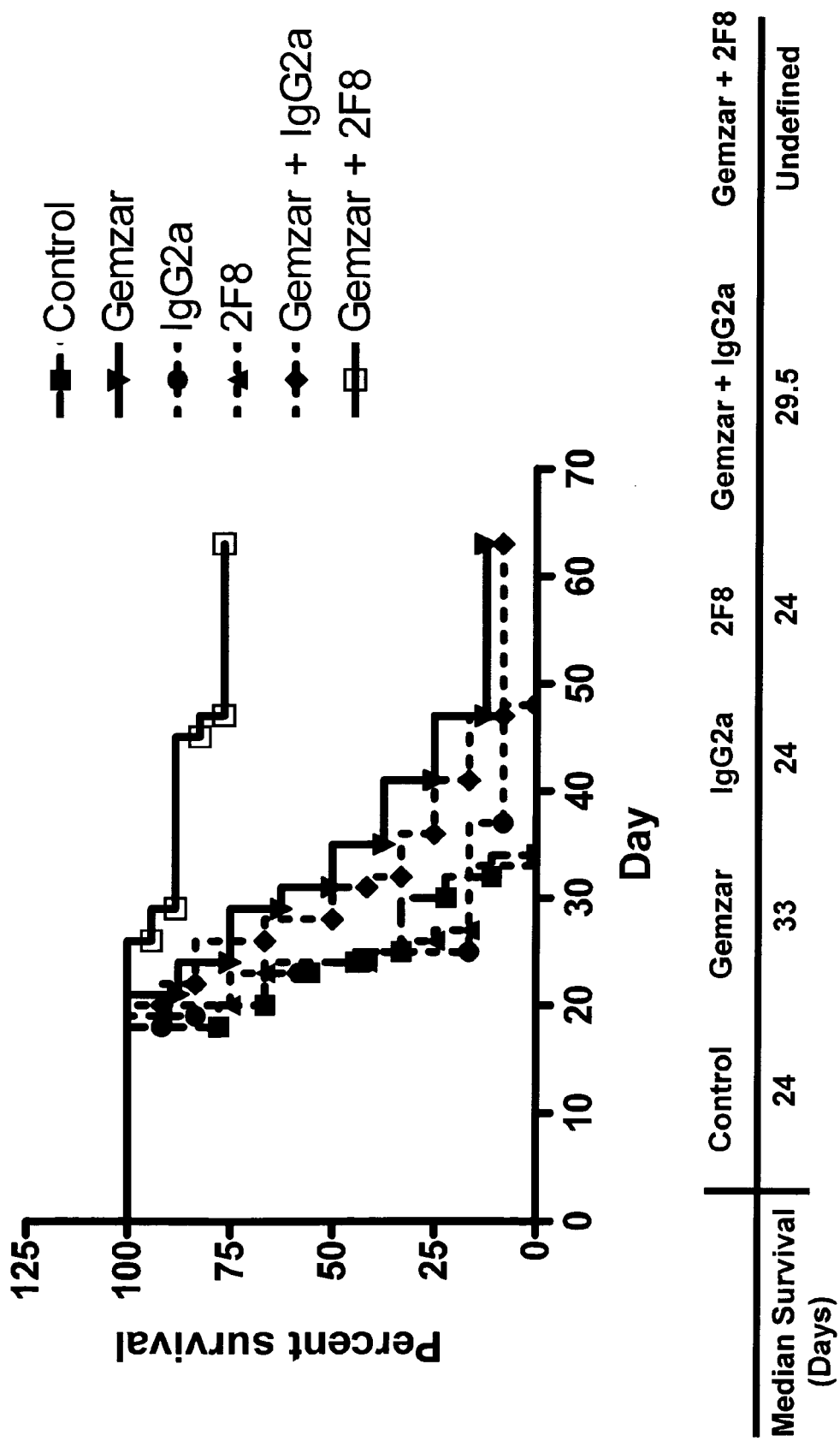
FIG. 2 depicts a graph showing the effect of the nucleoside analog, gemcitabine (Gemzar) (80 mg/kg), in combination with the anti-GITR antibody, 2F8 (0.4 mg), on median survival time (Kaplan-Meier Survival Curve) over the course of treatment as compared to the effect of gemcitabine alone, 2F8 alone, and a vehicle control.

In addition, as shown in FIG. 2, the median survival for the IgG2a control mice and the mice treated with the GITR binding molecule alone was 24 days. Median survival was 31 days for the mice treated with Gemzar alone. All the Gemzar plus 2F8 treated mice were still alive at day 31 and the tumors were moderate in size.

In a second study, mice were injected in the tail vein with $1 \times 10^5$ CT26 cells and tumors were allowed to establish in the lung for 10 days. The animals were then divided into groups. One group of control mice was untreated. The group of mice receiving Gemzar was treated with 80 mg/kg Gemzar on Day 15. One group of mice received anti-GITR antibody (2F8) alone at a dose of 0.4 mg (I.P.) on Days 15, 16 and 17. The group of mice receiving Gemzar+2F8 were given 80 mg/kg Gemzar on Day 15 and 0.4 mg of 2F8 (I.P.) on Day 16. The number of tumors was assessed on day 22.

Figure 3:
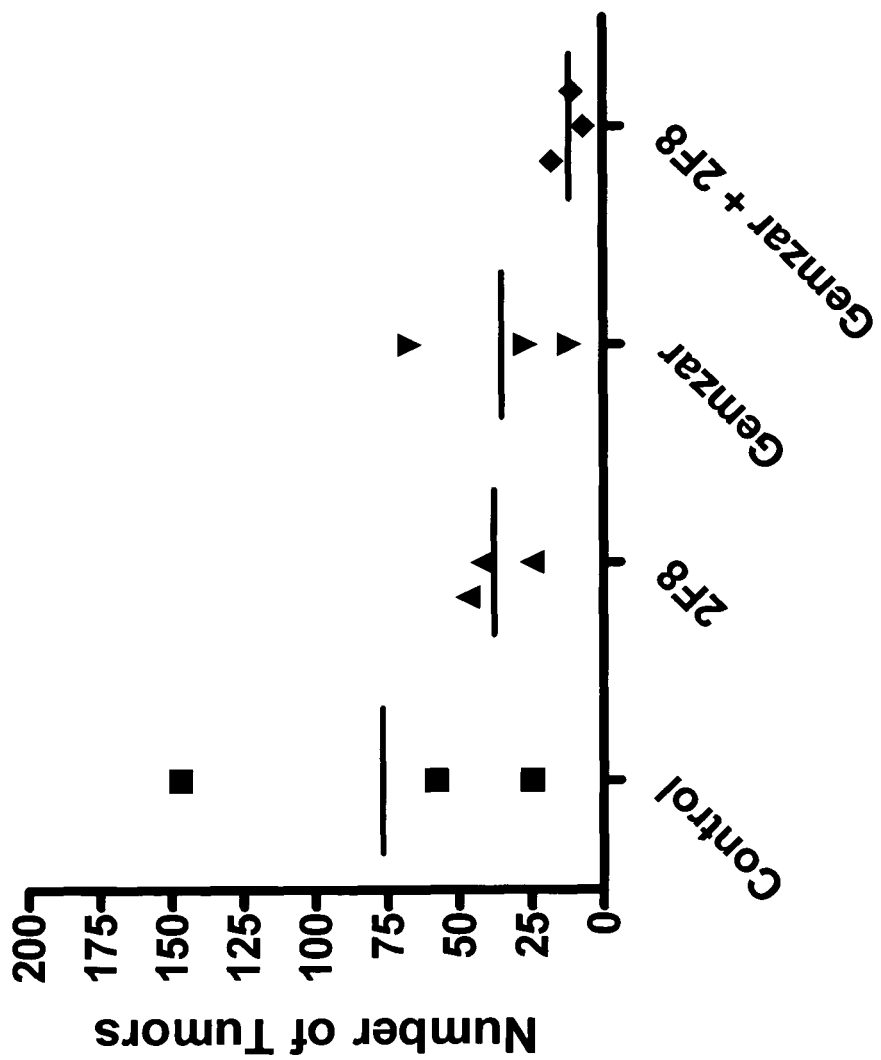
FIG. 3 depicts a graph showing the effect of the nucleoside analog, gemcitabine (Gemzar) (80 mg/kg), in combination with the anti-GITR antibody, 2F8 (0.4 mg), on the number of metastatic tumors over the course of treatment as compared to the effect of gemcitabine alone, 2F8 alone, and a vehicle control.

As shown in FIG. 3, the number of tumors in mice treated with the combination of Gemzar and 2F8 was reduced as compared to the number of tumors in mice treated with vehicle, Gemzar alone, or 2F8 alone.

Example 2

The Combination of a GITR Binding Molecule and an Agent that Affects Microtubule Formation Decreases Tumor Burden in an Animal Model of Melanoma Mice were injected in the flank with $12 \times 10^3$ B16 melanoma cells and divided into groups. One group of control mice was untreated. The group of mice receiving Taxol® was treated with 10 mg/kg Taxol® on Day 20 when tumors were approximately 100 mm$^3$. One group of mice received anti-GITR antibody (2F8) alone at a dose of 0.4 mg (I.P.) on Day 21. The group of mice receiving Taxol®+2F8 were given 10 mg/kg Taxol® on Day 20 and 0.4 mg of 2F8 (I.P.) on Day 21.

The size of the tumors and the survival of the mice were monitored. Tumors were measured using calipers, and tumor size was calculated using the formula $(L \times W^2)/2$.

Figure 4:
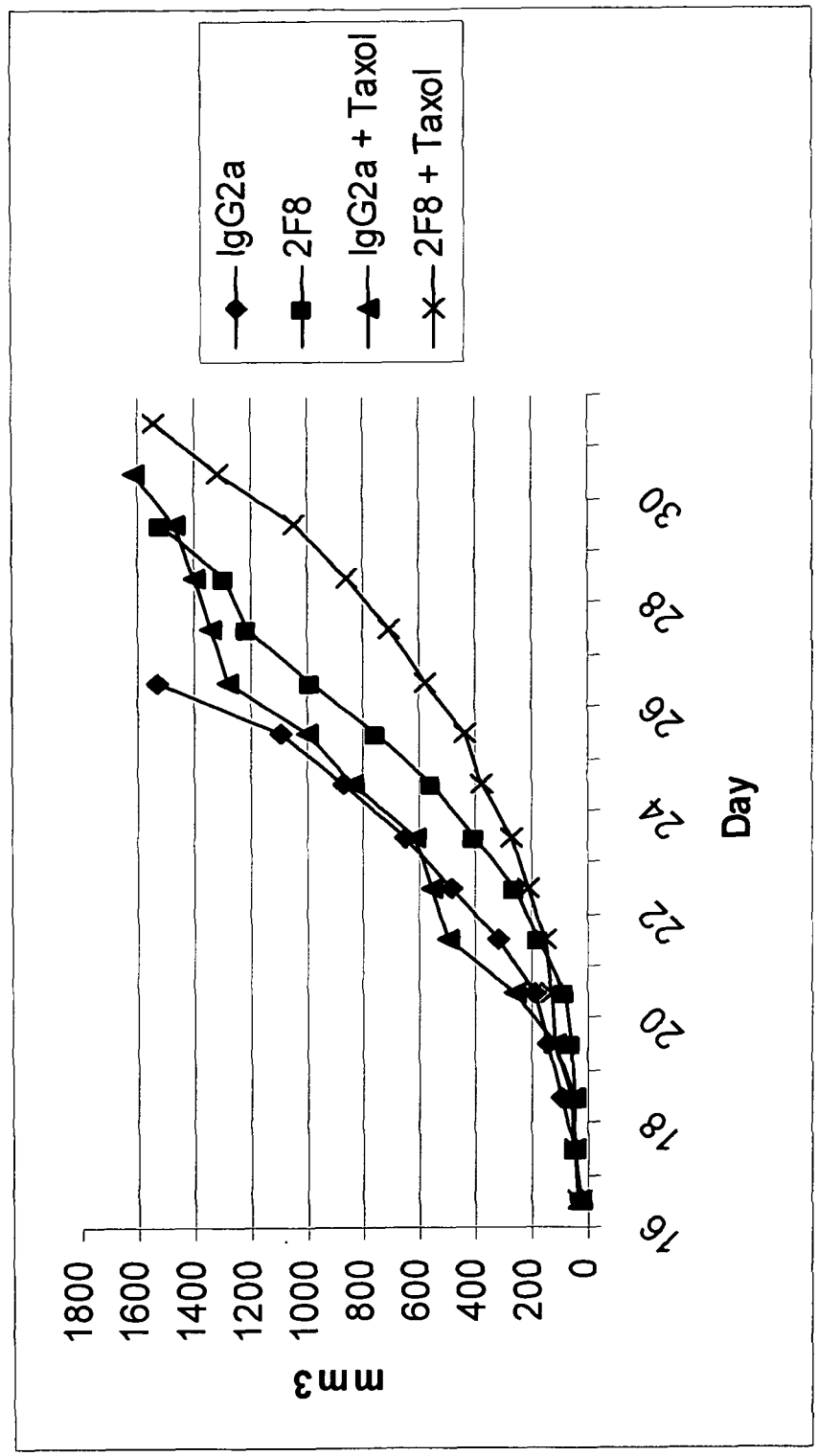
FIG. 4 depicts a graph showing the effect of an agent that affects microtubule formation, paclitaxel (Taxol®) (10 mg/kg), in combination with the anti-GITR antibody, 2F8 (0.4 mg), tumor volume over the course of treatment as compared to the effect of paclitaxel alone, 2F8 alone, and a vehicle control.

As shown in FIG. 4, the tumor burden in mice treated with the combination of Taxol® and 2F8 was reduced as compared to the tumor burden of mice treated with vehicle, Taxol® alone, or 2F8 alone.

Example 3

The Combination of a GITR Binding Molecule and an Alkylating Agent Decreases Tumor Burden in an Animal Model of Colon Carcinoma Mice were injected subcutaneously with $1 \times 10^5$ CT26 cells and divided into groups. One group of control mice was untreated. The group of mice receiving Cytoxan was treated with 150 mg/kg Cytoxan on Day 13. One group of mice received anti-GITR antibody (2F8) alone at a dose of 0.4 mg (I.P.) on Day 14. The group of mice receiving Cytoxan+2F8 were given 150 mg/kg Cytoxan® on Day 13 and 0.4 mg of 2F8 (I.P.) on Day 14.

The size of the tumors and the survival of the mice were monitored. Tumors were measured using calipers, and tumor size was calculated using the formula $(L \times W^2)/2$.

Figure 5:
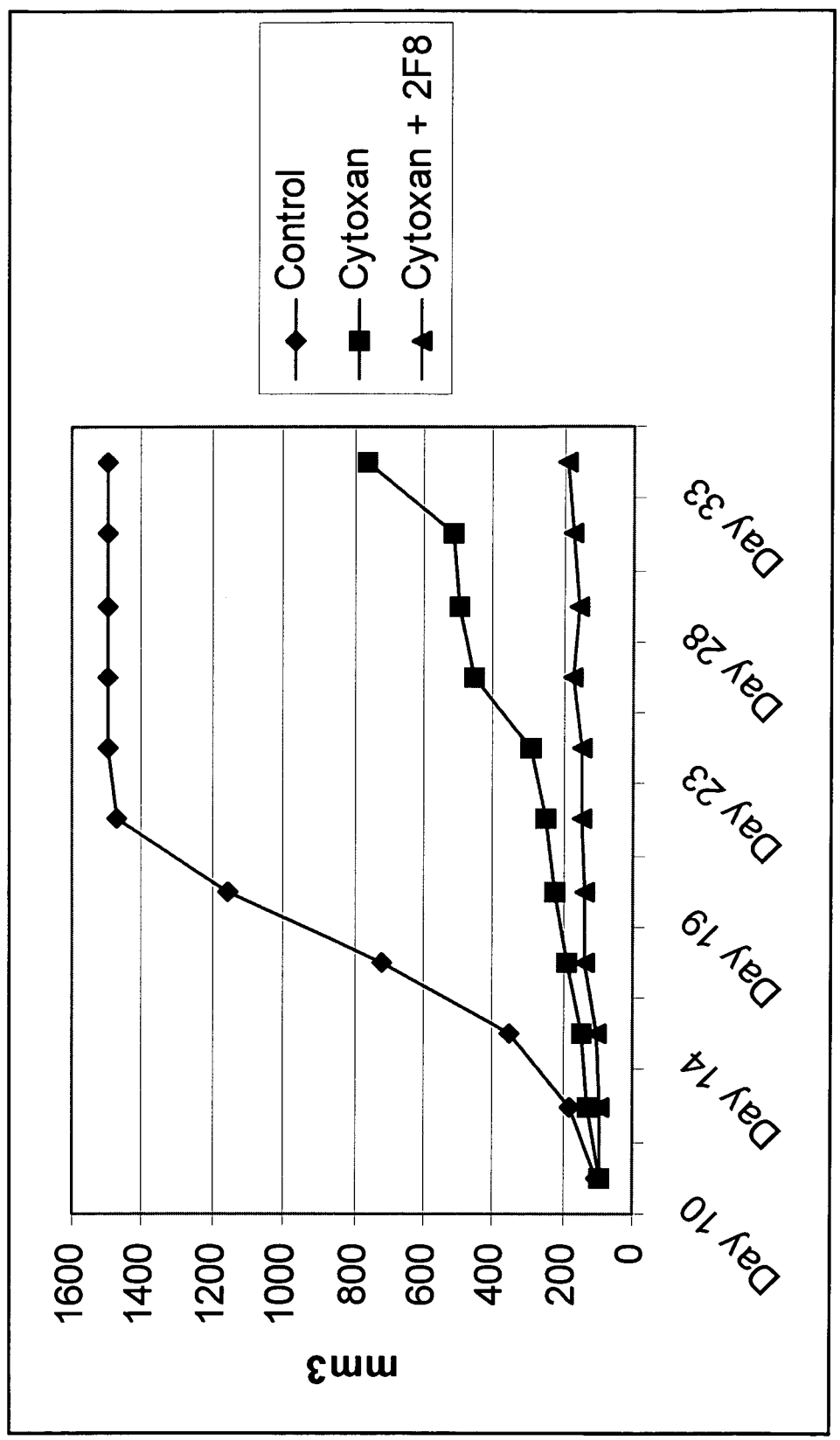
FIG. 5 depicts a graph showing the effect of the alkylating agent, cyclophosphamide (Cytoxan) (150 mg/kg), in combination with the anti-GITR antibody, 2F8 (0.4 mg), on tumor volume over the course of treatment as compared to the effect of cyclophosphamide alone, and a vehicle control.

As shown in FIG. 5, the tumor burden in mice treated with the combination of Cytoxan and 2F8 was reduced as compared to the tumor burden of mice treated with vehicle or Cytoxan alone.

Example 4

An Animal Model of Colon Carcinoma Treated with the Combination of a GITR Binding Molecule and an Alkylating Agent or a Nucleoside Analog Develop a Robust Memory Response to CT26 cells Mice treated as above in Examples 1 and 4 that had complete remission of their tumors were used in studies where they were injected with $3 \times 10^5$ CT26 cells IV (4 mice) or $10^6$ CT26 cells on their left flank and $10^6$ RENCA cells on their right flank (4 mice). Mice naïve to CT26 were used as controls. All 4 combination treated mice rejected the CT26 cell challenge and 2/4 completely rejected the RENCA cells. In the IV study, lungs were resected 14 days after injection of cells, stained with India ink and fixed with Fekete's Solution and analyzed for the presence of tumors; analysis of the lungs of all 4 animals showed no visible signs of tumors.

Example 5

The Combination of a GITR Binding Molecule and an Antimetabolite Decreases Tumor Burden in an Animal Model of Colon Carcinoma Mice were injected subcutaneously with $1 \times 10^5$ CT26 cells and divided into groups. One group of control mice was untreated. The group of mice receiving fluorouracil (5-FU) was treated with 75 mg/kg 5-FU on Day 10. The group of mice receiving 5-FU+2F8 were given 75 mg/kg 5-FU on Day 10 and 0.4 mg of 2F8 (I.P.) on Day 11.

The size of the tumors and the survival of the mice were monitored. Tumors were measured using calipers, and tumor size was calculated using the formula $(L \times W^2)/2$.

Figure 6:
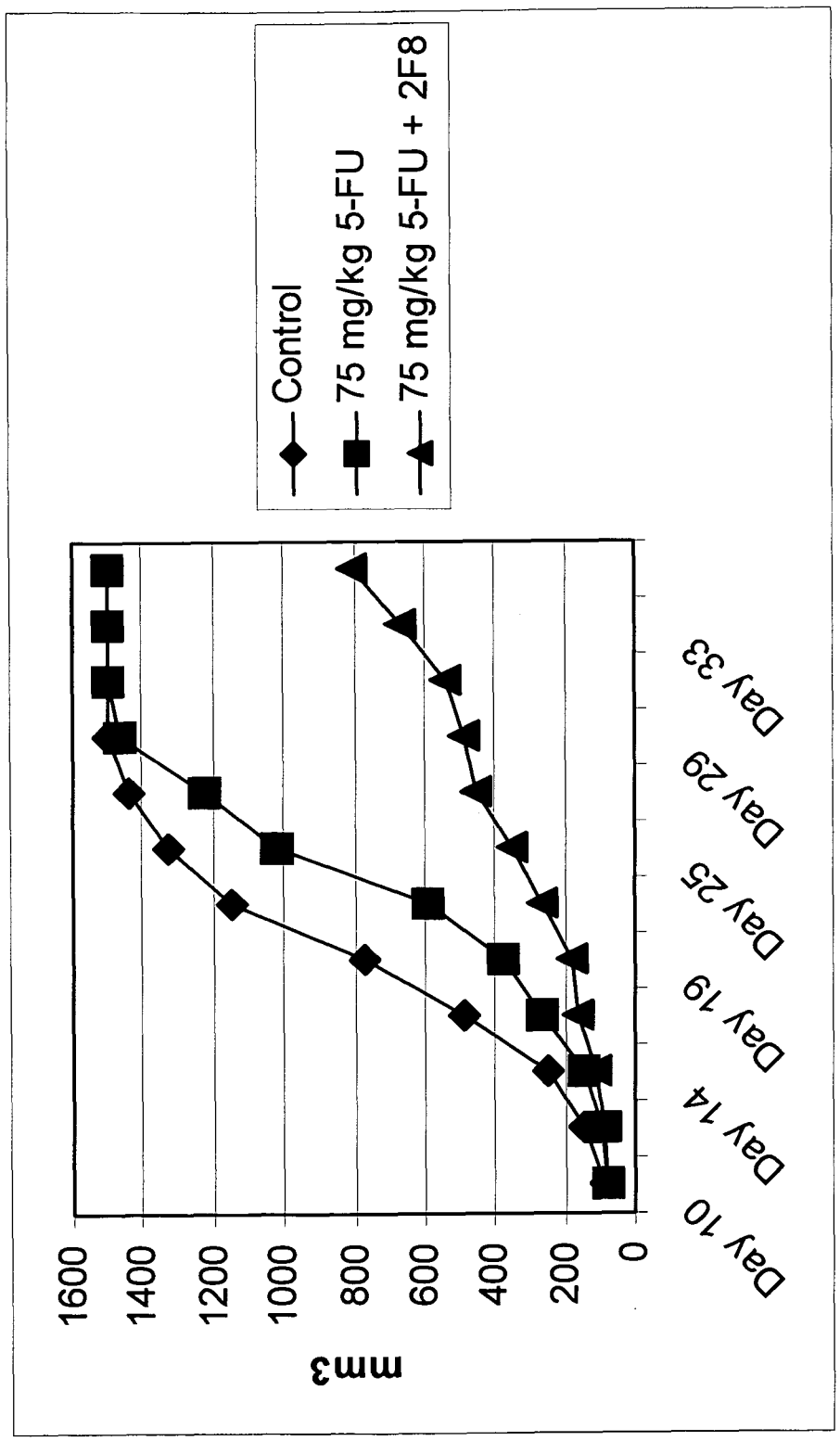
FIG. 6 depicts a graph showing the effect of the nucleoside analog, Fluorouracil (5-FU) (75 mg/kg), in combination with the anti-GITR antibody, 2F8 (0.4 mg), on tumor volume over the course of treatment as compared to the effect of Fluorouracil alone, and a vehicle control.

As shown in FIG. 6, the tumor burden in mice treated with the combination of 5-FU and 2F8 was reduced as compared to the tumor burden of mice treated with vehicle or 5-FU alone.

Example 6

The Combination of a GITR Binding Molecule and a Cytotoxic Antibiotic Decreases Tumor Burden in an Animal Model of Colon Carcinoma Mice were injected subcutaneously with $1 \times 10^5$ CT26 cells and divided into groups. One group of control mice was untreated. The group of mice receiving doxorubicin (Adriamycin) was treated with 5 mg/kg doxorubicin on Day 10. The group of mice receiving doxorubicin+2F8 were given 5 mg/kg doxorubicin on Day 10 and 0.4 mg of 2F8 (I.P.) on Day 11.

The size of the tumors and the survival of the mice were monitored. Tumors were measured using calipers, and tumor size was calculated using the formula $(L \times W^2)/2$.

Figure 7:
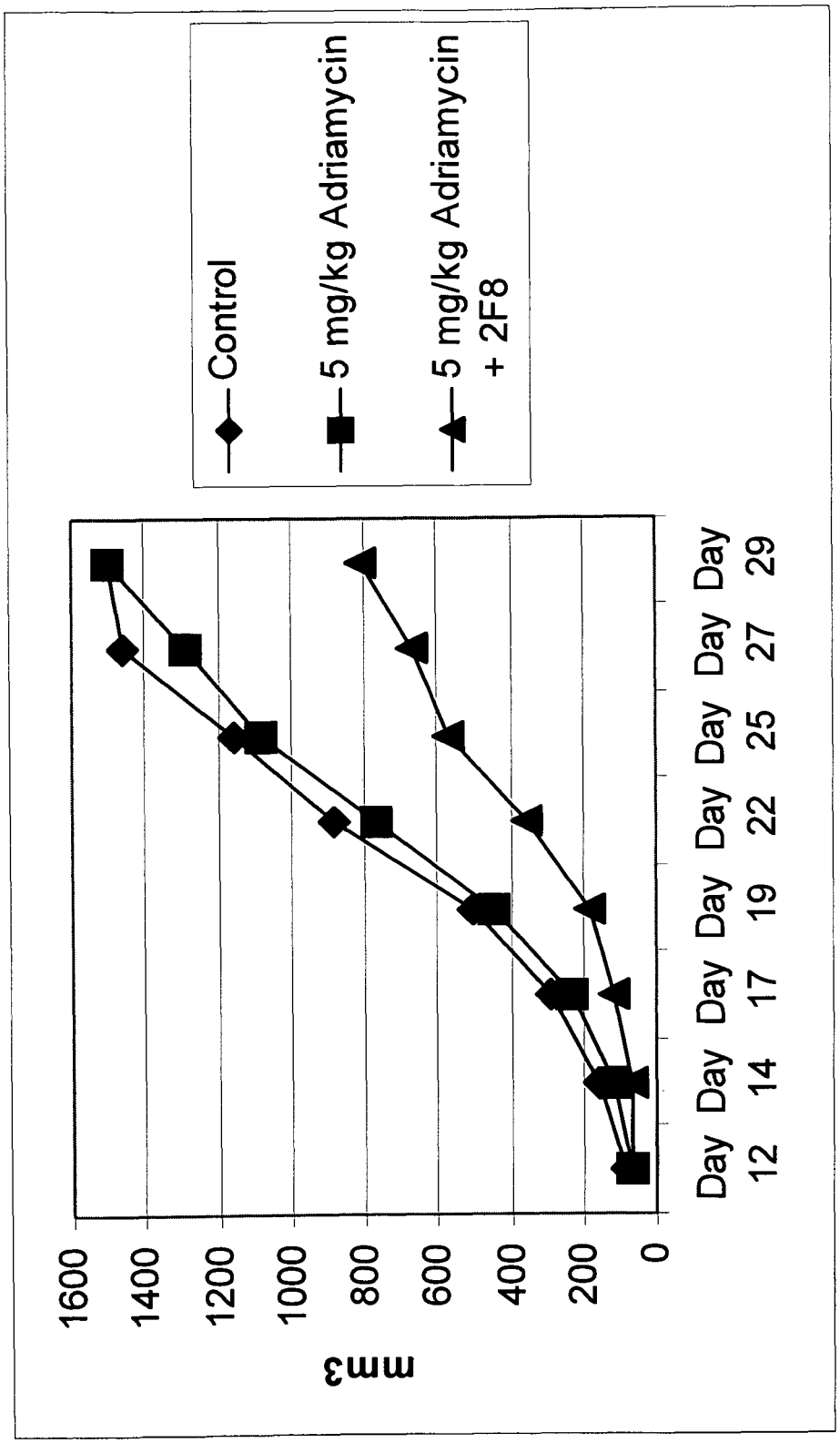
FIG. 7 depicts a graph showing the effect of the topoisomerase II inhibitor, doxorubicin (Adriamycin) (5 mg/kg), in combination with the anti-GITR antibody, 2F8 (0.4 mg), on tumor volume over the course of treatment as compared to the effect of Fluorouracil alone, and a vehicle control.

As shown in FIG. 7, the tumor burden in mice treated with the combination of doxorubicin and 2F8 was reduced as compared to the tumor burden of mice treated with vehicle or doxorubicin alone.

Example 7

The Combination of a GITR Binding Molecule and an Alkylating Agent Decreases Tumor Burden in an Animal Model of Melanoma Mice were injected subcutaneously with $1 \times 10^4$ B16 melanoma cells and divided into groups. One group of control mice was untreated. The group of mice receiving Cytoxan was treated with 150 mg/kg Cytoxan on Day 13. One group of mice received anti-GITR antibody (2F8) alone at a dose of 0.4 mg (I.P.) on Day 14. The group of mice receiving Cytoxan+2F8 were given 150 mg/kg Cytoxan® on Day 13 and 0.4 mg of 2F8 (I.P.) on Day 14.

The size of the tumors and the survival of the mice were monitored. Tumors were measured using calipers, and tumor size was calculated using the formula $(L \times W^2)/2$.

Figure 8:
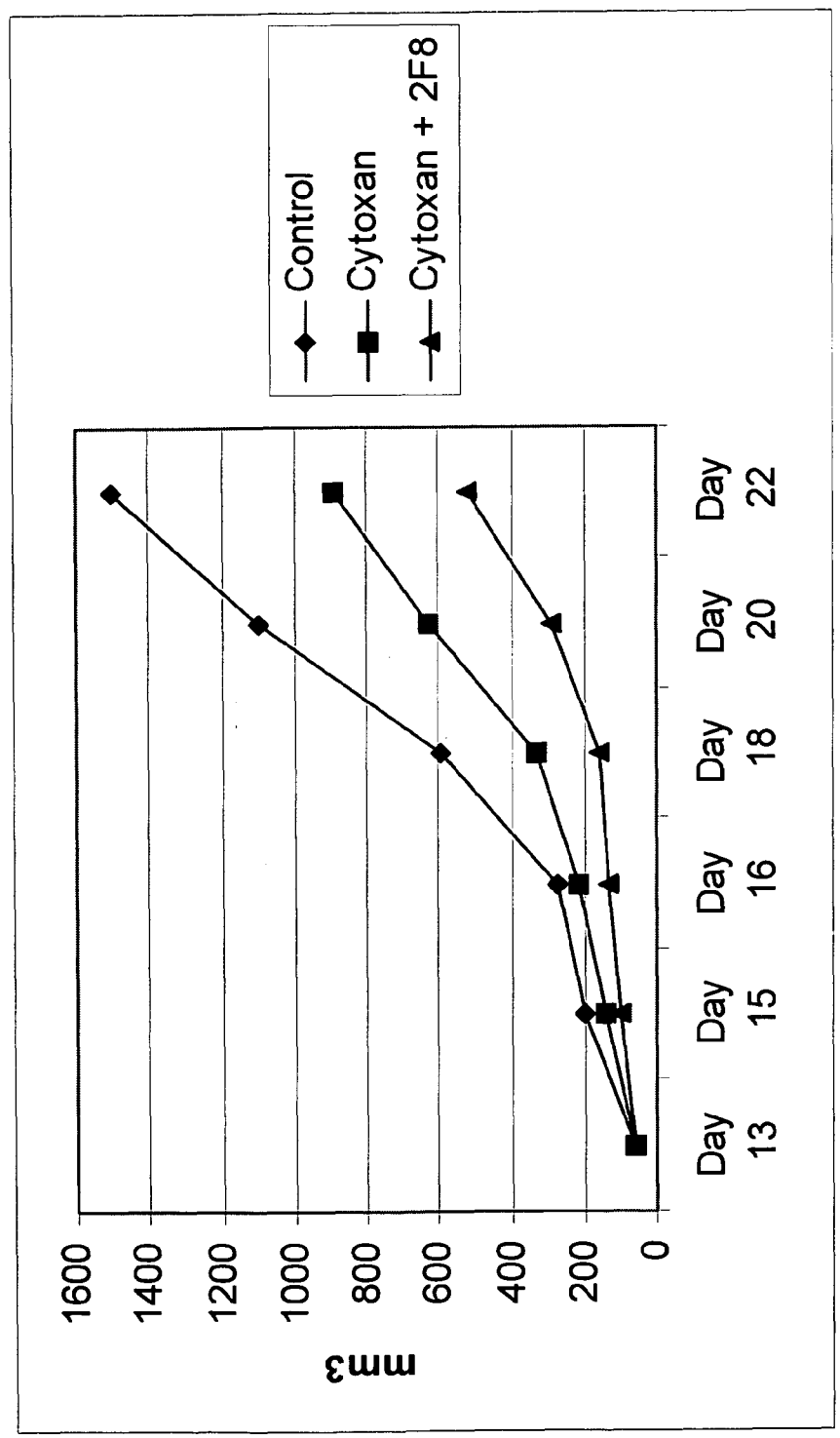
FIG. 8 depicts a graph showing the effect of the alkylating agent, cyclophosphamide (Cytoxan) (150 mg/kg), in combination with the anti-GITR antibody, 2F8 (0.4 mg), on tumor volume over the course of treatment as compared to the effect of cyclophosphamide alone, and a vehicle control.

As shown in FIG. 8, the tumor burden in mice treated with the combination of Cytoxan and 2F8 was reduced as compared to the tumor burden of mice treated with vehicle or Cytoxan alone.

EQUIVALENTS

Those skilled in the art will recognize, or be able to ascertain using no more than routine experimentation, many equivalents to the specific embodiments of the invention described herein. Such equivalents are intended to be encompassed by the following claims.

All publications and patents mentioned herein, including those items listed below, are hereby incorporated by reference in their entirety as if each individual publication or patent was specifically and individually indicated to be incorporated by reference.

What is claimed is:

1. A method for treating a subject having a tumor, the method comprising administering a GITR-binding antibody, or an antigen-binding fragment thereof, and a therapy, to the subject, wherein the GITR-binding antibody or the antigen-binding fragment acts as a GITR agonist, and the therapy is administered at a separate time from the GITR-binding antibody or the antigen-binding fragment at least once, and wherein the therapy is cytotoxic or exerts an anti-proliferative effect on cells.

2. The method of claim 1, wherein the method results in inhibition of tumor growth.

3. The method of claim 1, wherein the method results in reduction in tumor size.

4. The method of claim 1, wherein the method results in reduction in the number of tumors.

5. The method of claim 1, wherein the method decreases tumor burden in the subject.

6. The method of claim 1, wherein the method prolongs survival of the subject.

7. The method of any one of claims 1-6, wherein the separate in time administration comprises administration of the therapy to the subject prior to administration of the GITR-binding antibody or the antigen-binding fragment.

8. The method of any one of claims 1-6, wherein the GITR-binding antibody or the antigen-binding fragment acts synergistically with the therapy.

9. The method of claim 8, wherein the separate in time administration comprises administration of the therapy to the subject prior to administration of the GITR-binding antibody or the antigen-binding fragment.

10. The method of claim 1, wherein the GITR agonist activity of the GITR-binding antibody or the antigen-binding fragment comprises increasing T cell effector responses.

* * * * *

SEQUENCE LISTING

<160> NUMBER OF SEQ ID NOS: 7

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Phe Ser Leu Ser Thr Ser Gly Met Gly Val Gly
 1               5                  10

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

His Ile Trp Trp Asp Asp Asp Lys Tyr Tyr Asn Pro Ser Leu Lys Ser
 1               5                  10                  15

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic -continued

```
peptide

<400> SEQUENCE: 3

His Ile Trp Trp Asp Asp Lys Tyr Tyr Gln Pro Ser Leu Lys Ser
  1               5                  10                  15

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Thr Arg Arg Tyr Phe Pro Phe Ala Tyr
  1               5

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Ala Ser Gln Asn Val Gly Thr Asn Val Ala
  1               5                  10

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Ala Ser Tyr Arg Tyr Ser
  1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Gln Tyr Asn Thr Asp Pro Leu Thr
  1               5
```